United States Patent
Perkins et al.

(10) Patent No.: US 11,751,988 B2
(45) Date of Patent: Sep. 12, 2023

(54) MODULAR AORTIC ARCH PROSTHETIC ASSEMBLY AND METHOD OF USE THEREOF

(71) Applicant: Medtronic Vascular, Inc., Santa Rosa, CA (US)

(72) Inventors: Keith Perkins, Santa Rosa, CA (US); Dennis Brooks, Windsor, CA (US); Mark Stiger, Santa Rosa, CA (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 0 days.

(21) Appl. No.: 18/058,348

(22) Filed: Nov. 23, 2022

(65) Prior Publication Data
US 2023/0079152 A1 Mar. 16, 2023

Related U.S. Application Data

(63) Continuation of application No. 16/885,533, filed on May 28, 2020, now Pat. No. 11,534,285, which is a
(Continued)

(51) Int. Cl.
*A61F 2/07* (2013.01)
*A61F 2/852* (2013.01)
(Continued)

(52) U.S. Cl.
CPC ............ *A61F 2/07* (2013.01); *A61F 2/852* (2013.01); *A61F 2/954* (2013.01);
(Continued)

(58) Field of Classification Search
CPC ...... A61F 2/954; A61F 2002/061; A61F 2/07; A61F 2250/0065; A61F 2250/0039;
(Continued)

(56) References Cited

U.S. PATENT DOCUMENTS 6,645,242 B1   11/2003   Quinn et al.
6,814,752 B1   11/2004   Chuter
(Continued)

FOREIGN PATENT DOCUMENTS

CN   203280537 U   11/2013
CN   103476359 A   12/2013
(Continued)

OTHER PUBLICATIONS

PCT/US2017/064439, The International Search Report and the Written Opinion, dated Mar. 9, 2018, 15pgs.
(Continued)

*Primary Examiner* — Keri J Nelson
*Assistant Examiner* — Rebecca Lynee Zimmerman
(74) *Attorney, Agent, or Firm* — MEDLER FERRO WOODHOUSE & MILLS PLLC

(57) ABSTRACT

A prosthetic assembly configured for endovascular placement within an aortic arch and method of use thereof. The prosthetic assembly includes a proximal aortic stent-graft prosthesis configured to be positioned within a proximal portion of the aortic arch adjacent to the brachiocephalic artery, a distal aortic stent-graft prosthesis configured to be positioned within a distal portion of the aortic arch adjacent to the left subclavian artery, a first branch stent-graft prosthesis configured to be positioned within the brachiocephalic artery and a second branch stent-graft prosthesis configured to be positioned in one of the left common carotid and the left subclavian artery. When deployed, a proximal end of the first branch stent-graft prosthesis is disposed within a lumen of the proximal aortic stent-graft prosthesis to proximally displace the ostium of the brachiocephalic artery. When deployed, a proximal end of the distal aortic stent-graft prosthesis is disposed within the distal end of the proximal aortic stent-graft prosthesis to form an overlap between the
(Continued)

proximal and distal aortic stent-graft prostheses. The overlap is relatively increased by the first branch stent-graft prosthesis proximally displacing the ostium of the brachiocephalic artery.

20 Claims, 22 Drawing Sheets

Related U.S. Application Data continuation of application No. 15/830,221, filed on Dec. 4, 2017, now Pat. No. 10,702,369.

(60) Provisional application No. 62/430,218, filed on Dec. 5, 2016.

(51) Int. Cl.
 A61F 2/954 (2013.01)
 A61F 2/06 (2013.01)
 A61F 2/82 (2013.01)

(52) U.S. Cl.
 CPC ... *A61F 2002/061* (2013.01); *A61F 2002/067* (2013.01); *A61F 2002/068* (2013.01); *A61F 2002/075* (2013.01); *A61F 2002/826* (2013.01); *A61F 2210/0014* (2013.01); *A61F 2250/0039* (2013.01); *A61F 2250/0063* (2013.01); *A61F 2250/0065* (2013.01); *A61F 2250/0098* (2013.01)

(58) Field of Classification Search
 CPC ........ A61F 2250/0063; A61F 2002/826; A61F 2/852; A61F 2/06; A61F 2/856
 See application file for complete search history.

(56) References Cited

U.S. PATENT DOCUMENTS

| 8,092,511 | B2 | 1/2012 | Chuter |
| 8,211,158 | B2 | 7/2012 | Wolf |
| 8,747,455 | B2 | 6/2014 | Greenberg |
| 8,945,203 | B2 | 2/2015 | Shalev et al. |
| 9,839,542 | B2 | 12/2017 | Bruszewski et al. |
| 2008/0004687 | A1 | 1/2008 | Barbut et al. |
| 2011/0125244 | A1 | 5/2011 | Roeder et al. |
| 2012/0041544 | A1 | 2/2012 | Wolf |
| 2012/0271401 | A1 | 10/2012 | Bruszewski et al. |
| 2014/0316514 | A1* | 10/2014 | Zukowski ............... A61F 2/856 623/1.35 |
| 2020/0069445 | A1 | 3/2020 | Marmur et al. |

FOREIGN PATENT DOCUMENTS

| CN | 106029005 A | 10/2016 |
| FR | 2995206 A1 | 3/2014 |
| JP | 2014526929 A | 10/2014 |
| WO | 2013025727 A1 | 2/2013 |
| WO | 2014/0163957 A1 | 10/2014 |

OTHER PUBLICATIONS

Moulakakis, Konstantinos G., et al., The Chimney-Grail Technique for Preserving Supra-Aortic Branches: A Review Ann Cardiothorac Surg, www.annalscts.com, 2013;2(3):339-346.

Hogendoom, Wouter MD, et al., "Thoracic Endovascular Aortic Repair With the Chimney Grail Technique" Journal of Vascular Surgery, Aug. 2013, vol. 58, No. 2, pp. 502-511.

https ://ir.uiowa edu/cgi/viewcontent.cgi ?article=3534&context= etd (Year: 2012).

Modeling of the radial compressive properties of an aortic stent graft, Chaid Daniel Schwarz (2012).

* cited by examiner

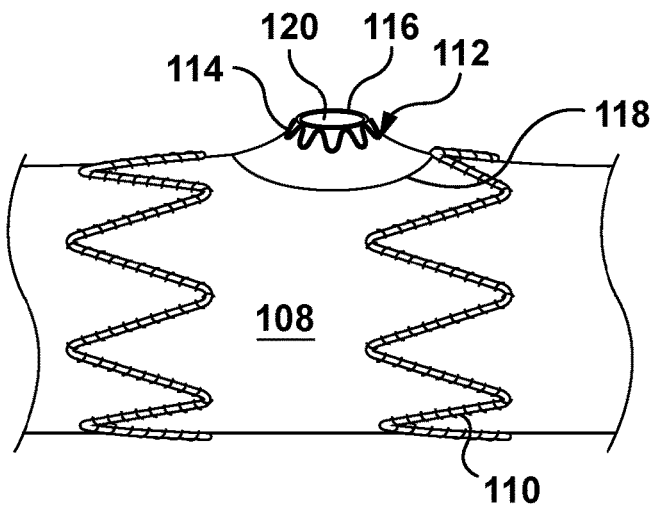
FIG. 8
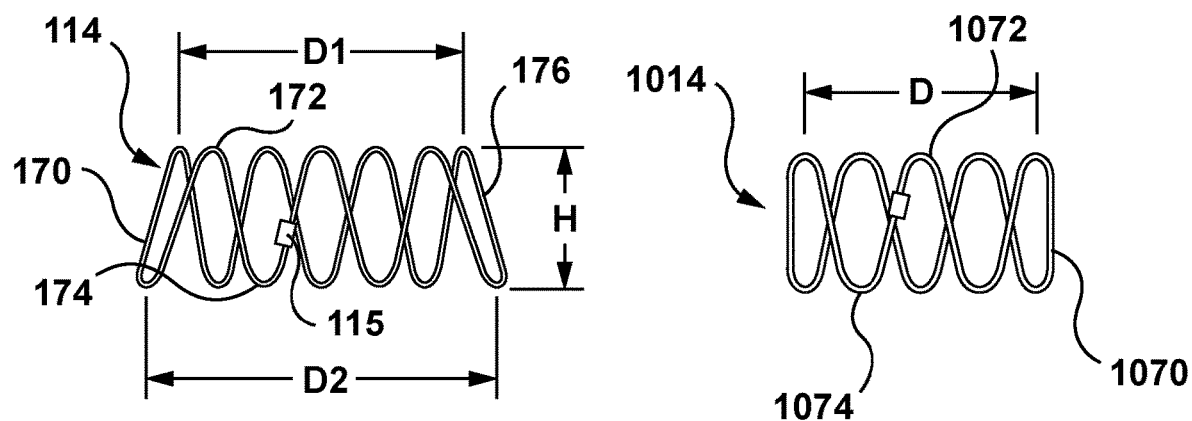
FIG. 9
FIG. 10

MODULAR AORTIC ARCH PROSTHETIC ASSEMBLY AND METHOD OF USE THEREOF

CROSS REFERENCE TO RELATED APPLICATIONS

This application is a continuation of U.S. application Ser. No. 16/885,533, filed May 28, 2020, which is a continuation of U.S. application Ser. No. 15/830,221, filed Dec. 4, 2017, which claims the benefit under 35 U.S.C. § 119(e) of the filing date of U.S. Provisional Application No. 62/430,218 filed Dec. 5, 2016, the disclosures of which are each herein incorporated by reference in their entirety.

FIELD OF THE INVENTION

This invention relates generally to endoluminal medical devices and procedures, and more particularly to a modular assembly or system configured to perfuse the aortic arch via an endovascular approach.

BACKGROUND OF THE INVENTION

Aneurysms, dissections, penetrating ulcers, intramural hematomas and/or transections may occur in blood vessels, and most typically occur in the aorta and peripheral arteries. Depending on the region of the aorta involved, the aneurysm may extend into areas having vessel bifurcations or segments of the aorta from which smaller "branch" arteries extend. Various types of aortic aneurysms may be classified on the basis of the region of aneurysmal involvement. For example, thoracic aortic aneurysms include aneurysms present in the ascending thoracic aorta, the aortic arch, and branch arteries that emanate therefrom, such as subclavian arteries, and also include aneurysms present in the descending thoracic aorta and branch arteries that emanate therefrom, such as thoracic intercostal arteries and/or the suprarenal abdominal aorta and branch arteries that emanate therefrom, such as superior mesenteric, celiac and/or intercostal arteries. Lastly, abdominal aortic aneurysms include aneurysms present in the aorta below the diaphragm, e.g., pararenal aorta and the branch arteries that emanate therefrom, such as the renal arteries.

The thoracic aorta has numerous arterial branches. The arch of the aorta has three major branches extending therefrom, all of which usually arise from the convex upper surface of the arch and ascend through the superior thoracic aperture. The brachiocephalic artery originates anterior to the trachea. The brachiocephalic artery (BCA) divides into two branches, the right subclavian artery (which supplies blood to the right arm) and the right common carotid artery (which supplies blood to the right side of the head and neck). The left common carotid (LCC) artery arises from the arch of the aorta just to the left of the origin of the brachiocephalic artery. The left common carotid artery supplies blood to the left side of the head and neck. The third branch arising from the aortic arch, the left subclavian artery (LSA), originates behind and just to the left of the origin of the left common carotid artery and supplies blood to the left arm. However, a significant proportion of the population has only two great branch vessels coming off the aortic arch while others have four great branch vessels coming of the aortic arch. As will be explained in more detail herein, the distance(s) between the great branch vessels varies considerably amongst patients and the anatomical variation of the aortic arch complicates treatment thereof.

For patients with thoracic aneurysms of the aortic arch, surgery to replace the aorta may be performed where the aorta is replaced with a fabric substitute in an operation that uses a heart-lung machine. In such a case, the aneurysmal portion of the aorta is removed or opened, and a substitute lumen is sewn across the aneurysmal portion to span it. Such surgery is highly invasive, requires an extended recovery period and, therefore cannot be performed on individuals in fragile health or with other contraindicative factors.

Alternatively, the aneurysmal region of the aorta can be bypassed by use of an endoluminally delivered tubular exclusion device, e.g., by a stent-graft placed inside the vessel spanning the aneurysmal portion of the vessel, to seal off the aneurysmal portion from further exposure to blood flowing through the aorta. A stent-graft can be implanted without a chest incision, using specialized catheters that are introduced through arteries, usually through incisions in the groin region of the patient. The use of stent-grafts to internally bypass, within the aorta or flow lumen, the aneurysmal site, is also not without challenges. In particular, where a stent-graft is used at a thoracic location, care must be taken so that critical branch arteries are not covered or occluded by the stent-graft yet the stent-graft must seal against the aorta wall and provide a flow conduit for blood to flow past the aneurysmal site. Where the aneurysm is located immediately adjacent to the branch arteries, there is a need to deploy the stent-graft in a location which partially or fully extends across the location of the origin of the branch arteries from the aorta to ensure sealing of the stent-graft to the artery wall.

To accommodate side branches, main vessel stent-grafts having a fenestration or opening in a side wall thereof may be used. The main vessel stent-graft is positioned to align its fenestration with the ostium of the branch vessel. In use, a proximal end of the stent-graft, having one or more side openings, is prepositioned and securely anchored in place so that its fenestrations or openings are oriented when deployed to avoid blocking or restricting blood flow into the side branches. Fenestrations by themselves do not form a tight seal or include discrete conduit(s) through which blood can be channeled into the adjacent side branch artery. As a result, blood leakage is prone to occur into the space between the outer surface of the main aortic stent-graft and the surrounding aortic wall between the edge of the graft material surrounding the fenestrations and the adjacent vessel wall. Similar blood leakage can result from post-implantation migration or movement of the stent-graft causing misalignment between the fenestration(s) and the branch artery(ies), which may also result in impaired flow into the branch artery(ies).

In some cases, the main vessel stent-graft is supplemented by another stent-graft, often referred to as a branch stent-graft. The branch stent-graft is deployed through the fenestration into the branch vessel to provide a conduit for blood flow into the branch vessel. The branch stent-graft is preferably sealingly connected to the main stent-graft in situ to prevent undesired leakage between it and the main stent-graft. This connection between the branch stent-graft and main stent-graft may be difficult to create effectively in situ and is a site for potential leakage.

In some instances, branch stent-grafts are incorporated into or integrally formed with the main stent-graft as extensions thereof. Such integral branch stent-grafts extensions are folded or collapsed against the main stent-graft for delivery and require complicated procedures, requiring multiple sleeves and guide wires, to direct the branch stent-grafts extension into the branch vessel and subsequently expand. Further, in some instances, such branch stent-grafts extensions tend to return to their folded or collapsed configuration, and thus do not provide an unobstructed flow path to the branch vessel. Because the position or location of integral branch stent-grafts extensions is fixed on the stent-graft, there is no opportunity to ensure that each integral branch stent-grafts extension is optimally aligned with their intended target branch ostium. Offset alignment between the integral branch stent-grafts extension and target branch can make cannulation and branch stent-graft deployment difficult and put the patient at risk for occlusive stroke. Thus, integral branch stent-grafts extensions are not optimized to treat all patient anatomical variations which significantly limit patient applicability for these designs.

Another approach for treating variations in patient anatomy is utilization of a custom designed endovascular stent-graft. However, custom designed stent-grafts require a significant lead time, i.e., 6-8 weeks, and are costly to design and manufacture.

Thus, there remains a need in the art for improvements in stent-graft structures for directing flow from a main vessel, such as the aorta, into branch vessels emanating therefrom, such as branch vessels of the aortic arch.

BRIEF SUMMARY OF THE INVENTION

Embodiments hereof relate to a prosthetic assembly configured for endovascular placement within an aortic arch, the prosthetic assembly including a proximal aortic stent-graft prosthesis, a distal aortic stent-graft prosthesis, a first branch stent-graft prosthesis and a second branch stent-graft prosthesis. The proximal aortic stent-graft prosthesis includes a tubular graft, at least one stent coupled to the tubular graft, and a coupling extending from the tubular graft. The coupling is configured to be positioned proximal to an ostium of a first branch vessel when deployed in situ. The distal aortic stent-graft prosthesis includes a tubular graft, at least one stent coupled to the tubular graft, and a coupling extending from the tubular graft. The first branch stent-graft prosthesis includes a tubular graft and at least one stent coupled to the tubular graft, and the first branch stent-graft prosthesis is configured to be disposed through the coupling of the proximal aortic stent-graft prosthesis when the proximal aortic stent-graft prosthesis and the first branch stent-graft prosthesis are each in an expanded configuration. The second branch stent-graft prosthesis including a tubular graft and at least one stent coupled to the tubular graft, and the second branch stent-graft prosthesis is configured to be disposed through the coupling of the distal aortic stent-graft prosthesis when the distal aortic stent-graft prosthesis and the second branch stent-graft prosthesis are each in an expanded configuration. A proximal end of the distal aortic stent-graft prosthesis is configured to be disposed within a distal end of the proximal aortic stent-graft prosthesis to form an overlap between the proximal and distal aortic stent-graft prostheses when the proximal and distal aortic stent-graft prostheses are in their respective expanded configurations. The overlap is relatively increased due to the coupling of the proximal aortic stent-graft prosthesis being positioned proximal to the ostium of the first branch vessel in situ.

In an embodiment hereof, the proximal aortic stent-graft prosthesis is configured to be positioned within a proximal portion of the aortic arch adjacent to the brachiocephalic artery, the distal aortic stent-graft prosthesis is configured to be positioned within a distal portion of the aortic arch adjacent to the left subclavian artery, the first branch stent-graft prosthesis is configured to be positioned within the brachiocephalic artery, and the second branch stent-graft prosthesis is configured to be positioned in one of the left common carotid and the left subclavian artery.

In an embodiment hereof, the proximal aortic stent-graft prosthesis includes a tubular graft, at least one stent coupled to the tubular graft, and a coupling extending from the tubular graft. The distal aortic stent-graft prosthesis includes a tubular graft, at least one stent coupled to the tubular graft, and a coupling extending from the tubular graft. The first branch stent-graft prosthesis includes a tubular graft and at least one stent coupled to the tubular graft, and the first branch stent-graft prosthesis is configured to be disposed through the coupling of the proximal aortic stent-graft prosthesis when the proximal aortic stent-graft prosthesis and the first branch stent-graft prosthesis are each in an expanded configuration. The second branch stent-graft prosthesis including a tubular graft and at least one stent coupled to the tubular graft, and the second branch stent-graft prosthesis is configured to be disposed through the coupling of the distal aortic stent-graft prosthesis when the distal aortic stent-graft prosthesis and the second branch stent-graft prosthesis are each in an expanded configuration. A proximal end of the distal aortic stent-graft prosthesis is configured to be disposed within a distal end of the proximal aortic stent-graft prosthesis to form an overlap between the proximal and distal aortic stent-graft prostheses when the proximal and distal aortic stent-graft prostheses are in their respective expanded configurations. A portion of the first branch stent-graft prosthesis in its expanded configuration extends along the overlap such that a proximal end of the first branch stent-graft prosthesis is positioned proximal to the overlap and effectively proximally reroutes an ostium of a first branch vessel in situ.

Embodiments hereof also relate a method of deploying a prosthetic assembly within an aortic arch. A proximal aortic stent-graft prosthesis is positioned within a proximal portion of the aortic arch adjacent to the brachiocephalic artery. The proximal aortic stent-graft prosthesis is in a compressed configuration for delivery. The proximal aortic stent-graft prosthesis is deployed into an expanded configuration. A first branch stent-graft prosthesis is positioned within the brachiocephalic artery and through a coupling of the proximal aortic stent-graft prosthesis. The first branch stent-graft prosthesis is in a compressed configuration for delivery. The first branch stent-graft prosthesis is deployed into an expanded configuration. A distal aortic stent-graft prosthesis is positioned within a distal portion of the aortic arch adjacent to the left subclavian artery. The distal aortic stent-graft prosthesis is in a compressed configuration for delivery. The distal aortic stent-graft prosthesis is expanded into an expanded configuration. A second branch stent-graft prosthesis is positioned within the left subclavian artery and through a coupling of the distal aortic stent-graft prosthesis. The second branch stent-graft prosthesis is in a compressed configuration for delivery. The second branch stent-graft prosthesis is deployed into an expanded configuration. A proximal end of the distal aortic stent-graft prosthesis is disposed within the distal end of the proximal aortic stent-graft prosthesis to form an overlap between the proximal and distal aortic stent-graft prostheses. The overlap is relatively increased by at least one of the first branch stent-graft prosthesis proximally displacing the ostium of the brachiocephalic artery and the second branch stent-graft prosthesis distally displacing the ostium of the left subclavian artery.

BRIEF DESCRIPTION OF DRAWINGS

FIG. 8 is a schematic close up illustration of a portion of the proximal aortic stent-graft prosthesis of FIG. 4, the proximal aortic stent-graft prosthesis having a coupling with a support wireform coupled thereto.

FIG. 9 is a schematic perspective view of the support wireform of FIG. 8 removed from the coupling.

FIG. 10 is a schematic perspective view of a support wireform according to another embodiment hereof.

DETAILED DESCRIPTION OF THE INVENTION

Specific embodiments are now described with reference to the figures, wherein like reference numbers indicate identical or functionally similar elements. Unless otherwise indicated, for the delivery system the terms "distal" and "proximal" are used in the following description with respect to a position or direction relative to the treating clinician. "Distal" and "distally" are positions distant from or in a direction away from the clinician, and "proximal" and "proximally" are positions near or in a direction toward the clinician. For the stent-graft devices "proximal" is the portion nearer the heart by way of blood flow path while "distal" is the portion of the stent-graft further from the heart by way of blood flow path.

The following detailed description is merely exemplary in nature and is not intended to limit the invention or the application and uses of the invention. Although the description of embodiments hereof is primarily in the context of modular devices for treating aneurysm disease within an aortic arch, the modular devices described herein can also be used to treat other aortic arch pathologies including but not limited to dissections, penetrating ulcers, intramural hematomas, transections, and pseudoaneurysms.

Furthermore, there is no intention to be bound by any expressed or implied theory presented in the preceding technical field, background, brief summary or the following detailed description.

Figure 1:
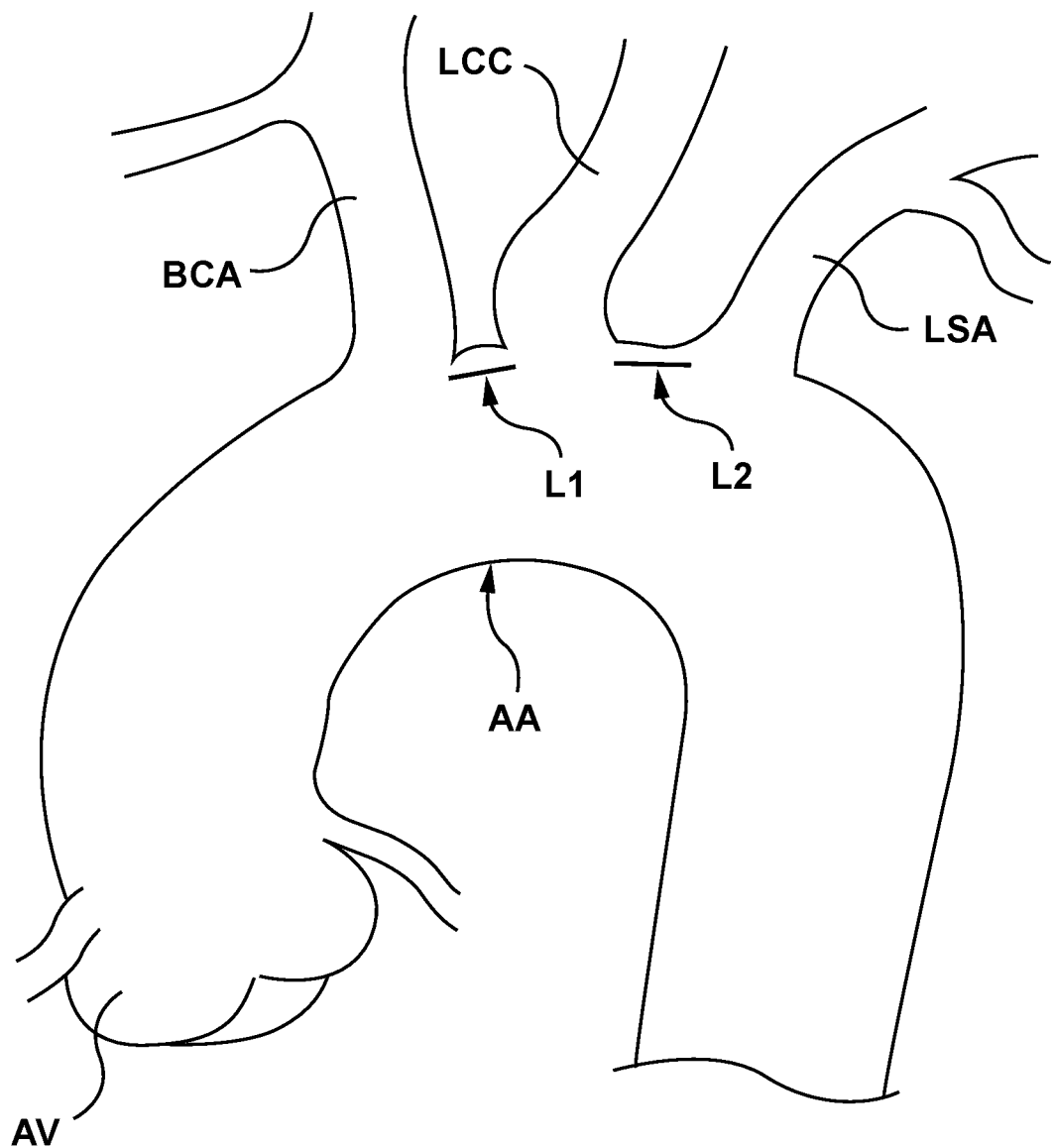
FIG. 1 is a schematic side view of an anatomy of an aortic arch.

Embodiments hereof relate to a modular assembly or system configured to perfuse the aortic arch via an endovascular approach. With reference to FIG. 1, which is a schematic side view of an anatomy of an aortic arch (labeled as "AA" in the figures), the challenge of using a modular assembly in the aortic arch is further described. More particularly, adoption of a modular approach has been limited by the short distances between the great branch vessels of the aortic arch. Landing zone L1 extends between the brachiocephalic artery (BCA) and the left common carotid (LCC), while landing zone L2 extends between the left common carotid (LCC) and the left subclavian artery (LSA). Both landing zones, L1 and L2, are insufficient for a durable and sufficient overlap of adjacent modular components that may be deployed within the aortic arch. Insufficient overlap of adjacent modular components would leave the modular system prone to development of leaks. The problem of separation of modular components is exacerbated by the dynamic environment of the aortic arch where there is extensive cardiac and respiratory induced motion.

Figure 2:
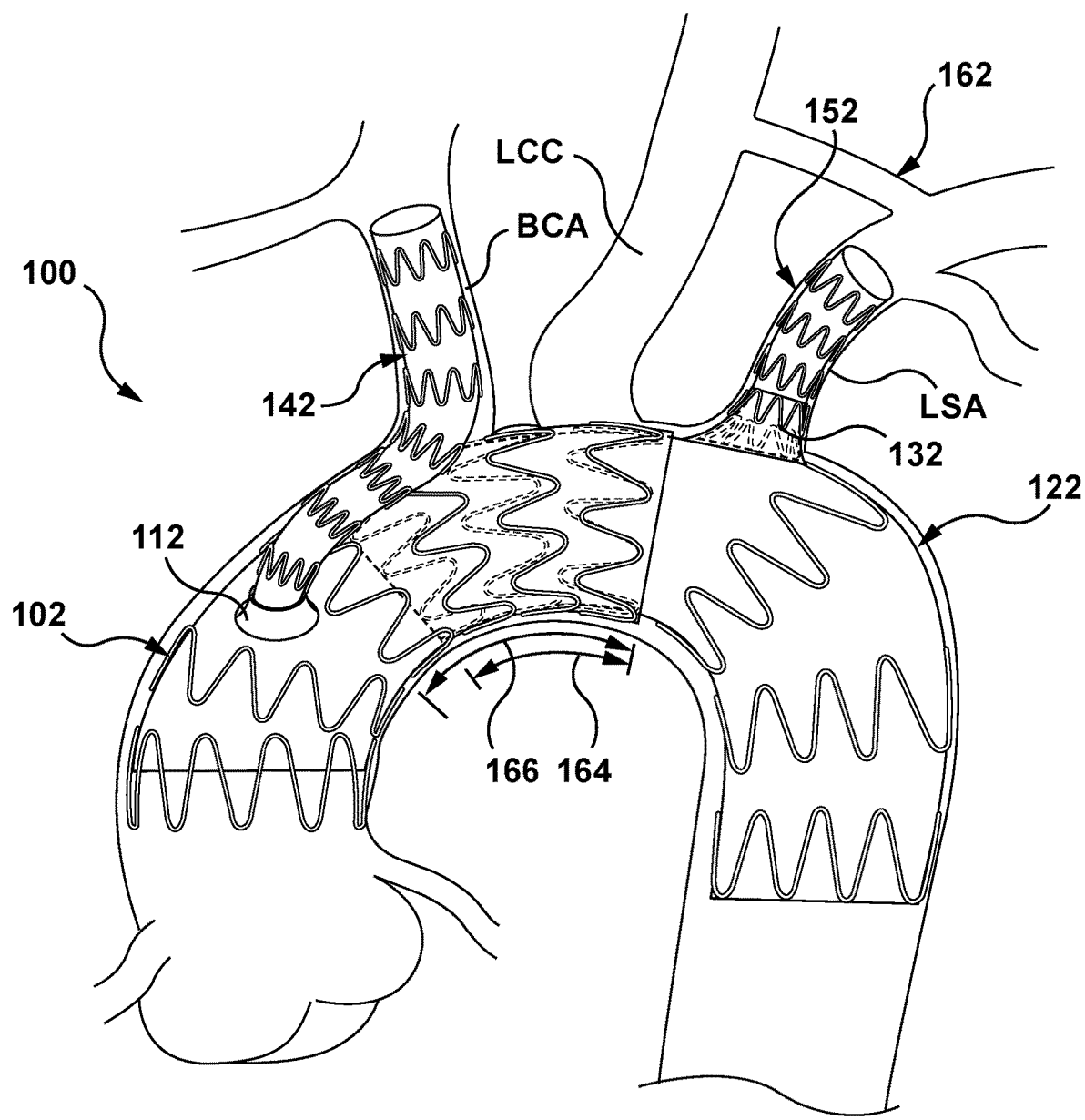
FIG. 2 is a schematic side view of an aortic arch prosthetic assembly according to an embodiment hereof, wherein the aortic arch prosthetic assembly is shown deployed and assembled in situ within an aortic arch.
Figure 3:
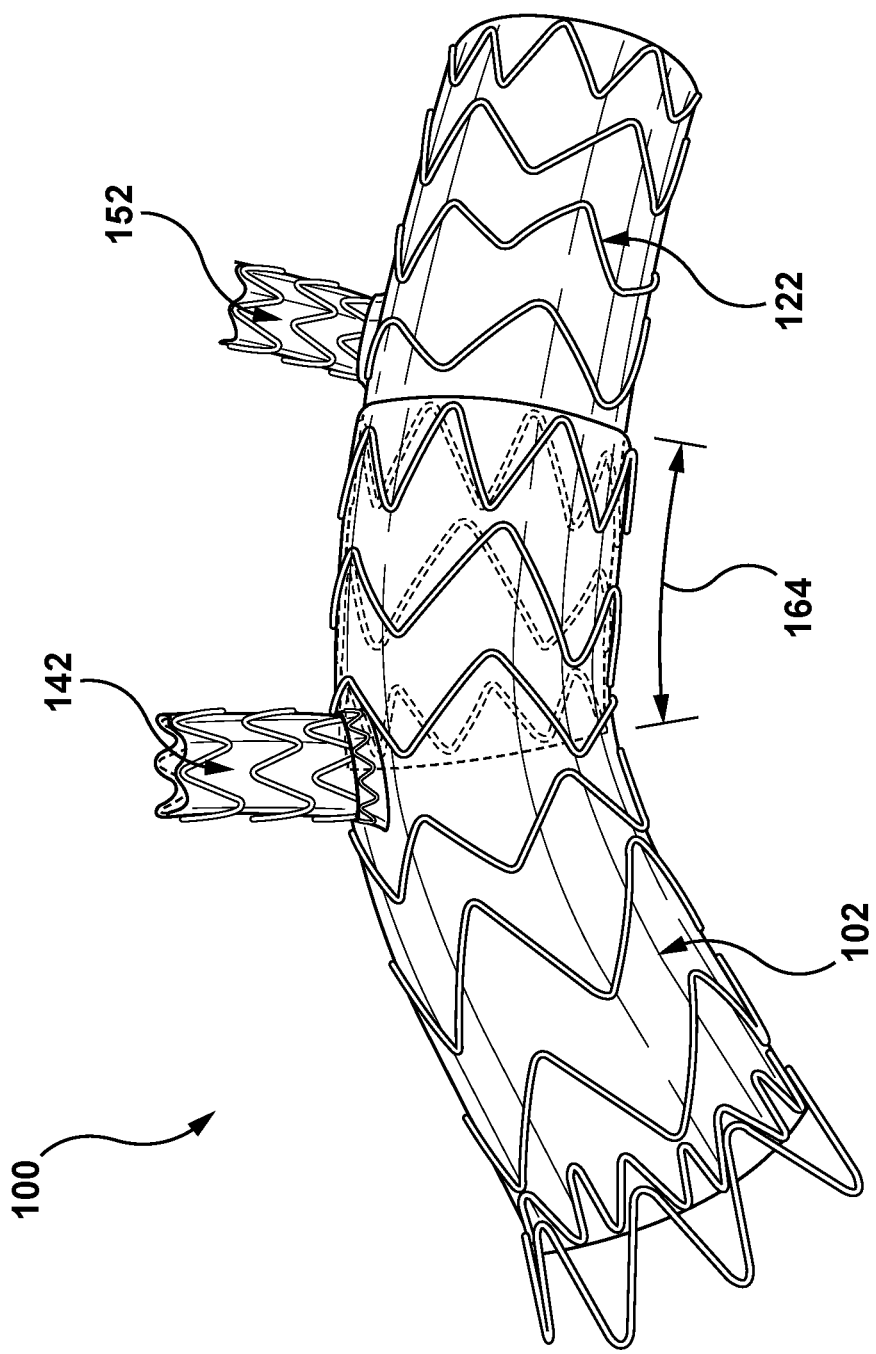
FIG. 3 is a side view of the aortic arch prosthetic assembly of FIG. 2, wherein the aortic arch prosthetic assembly is shown deployed and assembled but not in situ.

Embodiments hereof relate to an aortic arch prosthetic assembly 100 which is a modular assembly or system configured to perfuse the aortic arch and is configured to address the insufficient overlap issue that may be encountered by modular systems as described above. FIG. 2 illustrates an embodiment of aortic arch prosthetic assembly 100 in which a coupling 112 of a first or proximal aortic stent-graft prosthesis or module 102 is purposely positioned or configured to be positioned proximal to the ostium of the brachiocephalic artery to create or facilitate an adequate landing zone that permits sufficient overlap of adjacent modular components as will be explained in more detail herein. Aortic arch prosthetic assembly 100 is shown deployed and assembled in situ within an aortic arch in FIG. 2, and is shown deployed and assembled but not in situ in FIG. 3. Aortic arch prosthetic assembly 100 includes proximal aortic stent-graft prosthesis 102, a second or distal aortic stent-graft prosthesis or module 122, a first branch stent-graft prosthesis or module 142 extending from proximal aortic stent-graft prosthesis 102, and a second branch stent-graft prosthesis or module 152 extending from distal aortic stent-graft prosthesis 122. As will be explained in more detail, and as depicted in FIG. 2, proximal aortic stent-graft prosthesis 102 is configured for placement within a proximal portion of the aorta arch, adjacent to or proximal to the brachiocephalic artery, while distal aortic stent-graft prosthesis 122 is configured for placement within a distal portion of the aorta arch, adjacent to or distal to the left subclavian artery. First branch stent-graft prosthesis 142 is configured for placement within the brachiocephalic artery, and is configured to extend from within the brachiocephalic artery to coupling 112 of proximal aortic stent-graft prosthesis 102 which is purposely positioned or configured to be positioned proximal to the ostium of the brachiocephalic artery. In the embodiment of FIG. 2, a proximal portion of first branch stent-graft prosthesis 142 is configured for placement within the proximal portion of the aorta arch between an outer or exterior surface of proximal aortic stent-graft prosthesis 102 and the wall of the aorta. Second branch stent-graft prosthesis or module 152 is configured for placement in the left subclavian artery. The modular aspect of aortic arch prosthetic assembly 100 allows the interventionalist to treat each great vessel independently of the orientation of other target branch vessels and therefore aortic arch prosthetic assembly 100 is capable of treating a wider range of patient anatomies. More particularly, each module of aortic arch prosthetic assembly 100 is delivered independently of each other and thus each module can be optimized to conform to patient specific anatomical differences. Since each module of aortic arch prosthetic assembly 100 is delivered and deployed independently, each module can be aligned independently of each other and thus will result in higher levels of patient applicability. Further, the advantage of the modular approach of aortic arch prosthetic assembly 100 is that the amount of sufficient overlap between the proximal and distal aortic stent-graft prostheses 102, 122 can be adjusted as desired by varying or changing the amount of ostial displacement. Stated another way, the interventionalist may selectively move, adjust, or otherwise position proximal and/or distal aortic stent-graft prostheses 102, 122 as desired in order to achieve a sufficient overlap between the proximal and distal aortic stent-graft prostheses 102, 122. Thus, the modular aspect allows for aortic arch prosthetic assembly 100 to treat a variety of patients with a customizable or individualized approach but in an "off-the shelf" manner, i.e., with modular devices that are not custom designed for a particular patient's anatomy.

More particularly, aortic arch prosthetic assembly 100 is configured such that first branch stent-graft prosthesis 142 reroutes or displaces the ostium of the brachiocephalic artery to the ascending aorta towards or in the direction towards aortic valve AV (labeled in FIG. 1) so that distal aortic stent-graft prosthesis 122 can be deployed with a sufficient overlap 164 with respect to proximal aortic stent-graft prosthesis 102. Modular adjacent components such as proximal aortic stent-graft prosthesis 102 and distal aortic stent-graft prosthesis 122 require sufficient overlap 164 ranging between 10 mm and 50 mm to avoid endoleaks. Due to the curvature of the aortic arch, the amount of sufficient overlap may vary based on whether the measurements are along the inner aortic curve, the outer aortic curve, or the centerline of the aortic curve. By purposely positioning coupling 112 of proximal aortic stent-graft prosthesis 102 to be proximal to the ostium of the brachiocephalic artery when deployed in situ, first branch stent-graft prosthesis 142 reroutes or displaces the ostium of the brachiocephalic artery to the ascending aorta. As such, aortic arch prosthetic assembly 100 provides for an endovascular approach that creates or widens the distance for a landing zone 166 for the deployment of distal aortic stent-graft prosthesis 122. In this embodiment, landing zone 166 extends from the distal end of proximal aortic stent-graft prosthesis 102 to a proximal end of first branch stent-graft prosthesis 142 which extends through coupling 112 of proximal aortic stent-graft prosthesis 102. When being deployed, the proximal end of distal aortic stent-graft prosthesis 122 may be disposed anywhere within landing zone 166 provided that an adequate or sufficient overlap occurs to create a seal between proximal and distal aortic stent-graft prostheses 102, 122. Once the proximal end of distal aortic stent-graft prosthesis 122 is disposed and deployed within the distal end of proximal aortic stent-graft prosthesis 102, sufficient overlap 164 is created by the overlapping or overlaying portions of proximal and distal aortic stent-graft prostheses 102, 122. "Sufficient overlap" as used herein means that the overlapping or overlaying portions of proximal and distal aortic stent-graft prostheses 102, 122 are of a length sufficient or adequate to avoid endoleaks. As previously stated herein, the advantage of the modular approach of aortic arch prosthetic assembly 100 is that the amount of sufficient overlap between the proximal and distal aortic stent-graft prostheses 102, 122 can be adjusted as desired by varying or changing the amount of ostial displacement.

Another advantage of aortic arch prosthetic assembly 100 is that first branch stent-graft prosthesis 142 perfuses the brachiocephalic artery without impacting the proximal-most or seal stent of proximal aortic stent-graft prosthesis 102. Unlike a chimney stent-graft, which is external to a main stent-graft entirely to the proximal end of the main stent-graft, first branch stent-graft prosthesis 142 extends external to proximal aortic stent-graft prosthesis 102 but does not extend to or reach the proximal-most or seal stent of proximal aortic stent-graft prosthesis 102. Stated another way, as will be described in more detail herein, the proximal-most or seal stent of proximal aortic stent-graft prosthesis 102 is located proximal of the proximal end of first branch stent-graft prosthesis 142 and thus is not directly impacted by placement of first branch stent-graft prosthesis 142. Having a proximal-most or seal stent that is independent of the ostium of the brachiocephalic artery (as defined by the proximal end of first branch stent-graft prosthesis 142) has the added benefit of reducing the need for axial or rotational alignment of proximal aortic stent-graft prosthesis 102 which will lower the amount of manipulations required to deploy proximal aortic stent-graft prosthesis 102 and thus lower the risk for embolic stroke.

In the embodiment of FIG. 2, first branch stent-graft prosthesis 142 provides perfusion to the brachiocephalic artery, second branch stent-graft prosthesis 152 provides perfusion to the left subclavian artery, and a bypass or transposition 162 provides perfusion to the left common carotid artery. Left common carotid artery to left subclavian artery bypass 162 may be performed as needed to maintain perfusion to all the arch branch vessels and is considered an easier, less invasive procedure than other bypass procedures.

FIGS. 4-7 illustrate side views of proximal aortic stent-graft prosthesis 102, distal aortic stent-graft prosthesis 122, first branch stent-graft prosthesis 142, and second branch stent-graft prosthesis 152, respectively. Each module is shown in its deployed configuration and removed from aortic arch prosthetic assembly 100 for illustrative purposes, and each module will be described independently in turn.

Figure 4:
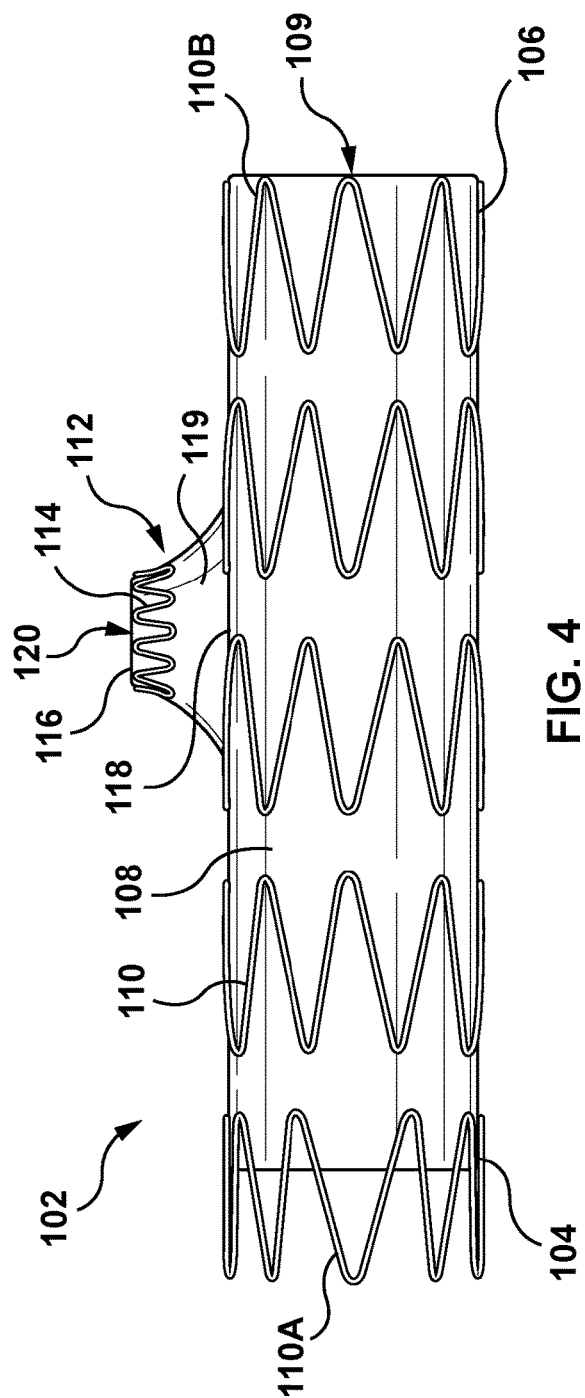
FIG. 4 is a schematic side view of a proximal aortic stent-graft prosthesis, the proximal aortic stent-graft prosthesis being a module or component of the aortic arch prosthetic assembly of FIG. 2, wherein the proximal aortic stent-graft prosthesis is shown deployed but not in situ.

With reference to FIG. 4, proximal aortic stent-graft prosthesis 102 is configured for placement in a proximal portion of the aorta arch, adjacent to the brachiocephalic artery, and/or into the ascending aorta proximal to the brachiocephalic artery. Proximal aortic stent-graft prosthesis 102 includes graft material 108 coupled to circumferential stents 110. Graft material 108 may be coupled to circumferential stents 110 using stitching or other means. In the embodiment shown in FIG. 4, circumferential stents 110 are coupled to an outside surface of graft material 108. However, circumferential stents 110 may alternatively be coupled to an inside surface of graft material 108. Although shown with five circumferential stents, it will be understood by one of ordinary skill in the art that proximal aortic stent-graft prosthesis 102 may include a greater or smaller number of stents depending upon the desired length of proximal aortic stent-graft prosthesis 102 and/or the intended application thereof. Graft material 108 may be any suitable graft material, for example and not limited to, woven polyester, DACRON® material, expanded polytetrafluoroethylene, polyurethane, silicone, electro spun materials, or other suitable materials. Circumferential stents 110 may be any conventional stent material or configuration. As shown, circumferential stents 110 are preferably made from a shape memory material, such as nickel-titanium alloy (nitinol), and are formed into a zig-zag configuration. The configuration of circumferential stents 110 is merely exemplary, and circumferential stents 110 may have any suitable configuration known in the art, including but not limiting to a continuous or non-continuous helical configuration. Proximal aortic stent-graft prosthesis 102 includes a proximal end 104 and a distal end 106. The stent which is disposed at proximal end 104 is referred to herein as the proximal-most stent 110A and may be generally described as an anchor stent or a seal stent in the art. In an embodiment hereof, as shown in FIG. 4, the proximal-most stent 110A extends outside of the graft material 108 in an open-web or uncovered configuration. Stent 110 which is disposed at distal end 106 is referred to herein as the distal-most stent 110<i>6</i> and may be generally described as an anchor stent or a seal stent in the art. The distal-most stent 110<i>6</i> extends only to the edge of the graft material 128 in a closed-web configuration as shown. In another embodiment hereof, the proximal-most stent 110A may extend only to the edge of the graft material 108 in a closed-web configuration and/or the distal-most stent 110<i>6</i> may extend outside of the graft material 108 in an open-web or uncovered configuration. Graft material 108 has a tubular configuration and as such defines a lumen 109 therethrough. Proximal aortic stent-graft prosthesis 102 further includes coupling 112, described in detail below with respect to FIGS. 8-11. Proximal aortic stent-graft prosthesis 102 may be similar to the Medtronic, Inc.'s VALIANT MONA LSA® thoracic stent-graft, or other known stent-grafts.

With additional reference to FIG. 8, coupling 112 is disposed on a midportion of proximal aortic stent-graft prosthesis 102 corresponding to an opening in graft material 108. In the embodiment of FIG. 2, as described above, coupling 112 is purposely positioned or configured to be positioned proximal to the ostium of the brachiocephalic artery when deployed in situ. For sake of illustration, coupling 112 is shown approximately in the middle of proximal aortic stent-graft prosthesis 102 but the location of coupling 112 may vary and coupling 112 may be disposed closer to proximal end 104 or may be disposed closer to distal end 106. In addition, for sake of illustration, coupling 112 is shown extending radially away from an outer surface of graft material 108 and thus may be considered an external coupling. However, coupling 112 may also be inverted so as to extend radially inward from an inner surface of graft material 108 and thus may be considered an internal coupling. Further, coupling 112 may be initially deployed in a first configuration, i.e., as an external coupling or an internal coupling, and may be displaced during positioning of a branch stent-graft prosthesis therethrough. Coupling 112 is generally frustoconically shaped. Coupling 112 is formed from graft material having a base 118 and a top 116. The graft material of coupling 112 is preferably the same type of graft material as graft material 108 and is preferably a continuation of graft material 108, although the coupling can be a separate piece of graft material attached to graft material 108. Although coupling 112 is described as generally frustoconical in shape, base 118 is preferably generally elliptical rather than circular. Base 118 may have, for example and not by way of limitation, a long axis of approximately 20-30 mm and a short axis of approximately 15-20 mm. Further, the height of coupling 112 may be approximately 10-40 mm. Further, since coupling 112 is configured to be used with first branch stent-graft prosthesis 142 which perfuses the brachiocephalic artery, the diameter of the top 116 may be approximately 8-20 mm.

A circumferential stent or annular support wireform 114 may be coupled to the graft material of coupling 112 around top 116. For description purposes, FIG. 9 illustrates support wireform 114 removed from coupling 112. Support wireform 114 may be formed from a tubular structure or wire 170 of a biocompatible resilient material such as nickel-titanium alloy (nitinol), MP35N spring wire, an acetal copolymer, or a polymeric material having shape memory characteristics. In another embodiment, support wireform 114 may be formed from a plastically deformable material. Further, in another embodiment, support wireform 114 may be laser cut. Support wireform 114 may be made from the same material as main body circumferential stents 110 or may be made from different material. For example, circumferential stents 110 may be balloon expandable and support wireform 114 may be self-expanding. Preferably, circumferential stents 110 and support wireform 114 are made from shape memory materials such as nitinol and are self-expanding. In various embodiments, wire 170 may be solid or hollow and have a circular cross-section. In an embodiment, wire 170 has a diameter between 0.008 inch and 0.012 inch, whereas circumferential stents 110 are generally about 0.010 inch to 0.021 inch in diameter. In one embodiment, the cross-section of wire 170 may be oval, square, rectangular, or any other suitable shape. As shown, wire 170 is shaped into a zig-zag or generally sinusoidal configuration having a plurality of opposing bends or crowns 172, 174 connecting generally straight segments or struts 176 together, and a crimp 115 connecting or coupling the two ends of wire 170 to form circumferential support wireform 114. Crowns 172 are disposed adjacent top 116 of coupling 112 and crowns 174 are disposed spaced from top 116. Support wireform 114 is oriented such that a longitudinal axis of support wireform 114 is generally co-linear with the longitudinal axis of coupling 112. In one embodiment, support wireform 114 includes eight crowns 172 and eight crowns 174 but it will be understood by those of ordinary skill in the art that the number of crowns is not limited. Support wireform 114 is coupled to coupling 112 using stitching or other means. Support wireform 114 may be coupled to an outside surface of coupling 112 to avoid the potential of metal-to-metal contact between support wireform 114 and circumferential stents 110 of proximal aortic stent-graft prosthesis 102 or support wireform 114 may alternatively be coupled to an inside surface of the graft material 128 of coupling 112.

In the embodiment of FIG. 9, support wireform 114 is generally frustoconically shaped. Crowns 172 of frustoconical support wireform 114 are symmetrically arranged in a circle having a first diameter D1 and crowns 174 of frustoconical support wireform 114 are arranged to be equally spaced around a circle having a second diameter D2 which is greater than diameter D1. Although support wireform 114 is described as generally frustoconical in shape, the base thereof may alternatively be elliptical rather than circular to more closely imitate the profile of coupling 112. If the base of support wireform 114 is elliptical, crowns 174 of frustoconical support wireform 114 are arranged to be equally spaced around an ovoid. The height H of support wireform 114, referring to the vertical or longitudinal distance between crowns 172 and crowns 174, may vary between 25% and 33% of the height of coupling 112. For example, for a coupling having a height between 12 mm and 15 mm, the height of support wireform 114 may be in the range of 3 mm and 5 mm. In another embodiment shown in FIG. 10, the support wireform may be generally cylindrical in shape rather than frustoconical. More specifically, a support wireform 1070 includes crowns 1072 that are symmetrically arranged in a circle having a diameter D and crowns 1074 of cylindrical support wireform 440 are arranged to be equally spaced around a circle also having diameter D.

Due to shape and material, coupling 112 has significant flexibility because the top of the coupling 112 when deployed can move longitudinally relative to the longitudinal axis of coupling 112. In particular, referring back to FIG. 4, coupling 112 includes an unsupported portion 119 of graft material 128 extending below support wireform 114 to base 118. Stated another way, coupling 112 is unsupported between crowns 174 and main proximal aortic stent-graft prosthesis 102. Unsupported portion 119 of graft material 128 does not have any inherent ability to position top 116 of coupling 112 as desired. However, support wireform 114 imparts structural integrity to the top 116 of coupling 112 to properly orient the top of coupling 112 as desired. The flexibility of coupling 112 and in particular the flexibility of unsupported portion 119 of graft material 128 allows for proximal aortic stent-graft prosthesis 102 to be rotationally offset up to and beyond 90 degrees without compromising flow through the branch stent-graft prosthesis to the target vessel. Accordingly, if proximal aortic stent-graft prosthesis 102 is not perfectly rotationally aligned with a branch vessel, coupling 112 can move or shift to cause top 116 to point towards the branch vessel. The mobility of coupling 112 thus reduces the requirement of precise targeting thereof while still allowing for perfusion of the branch vessel. Coupling 112 and variations thereof is further described in U.S. Patent Pub. No. 20120271401 to Bruszewski et al., assigned to the same assignee as the present disclosure.

Figure 5:
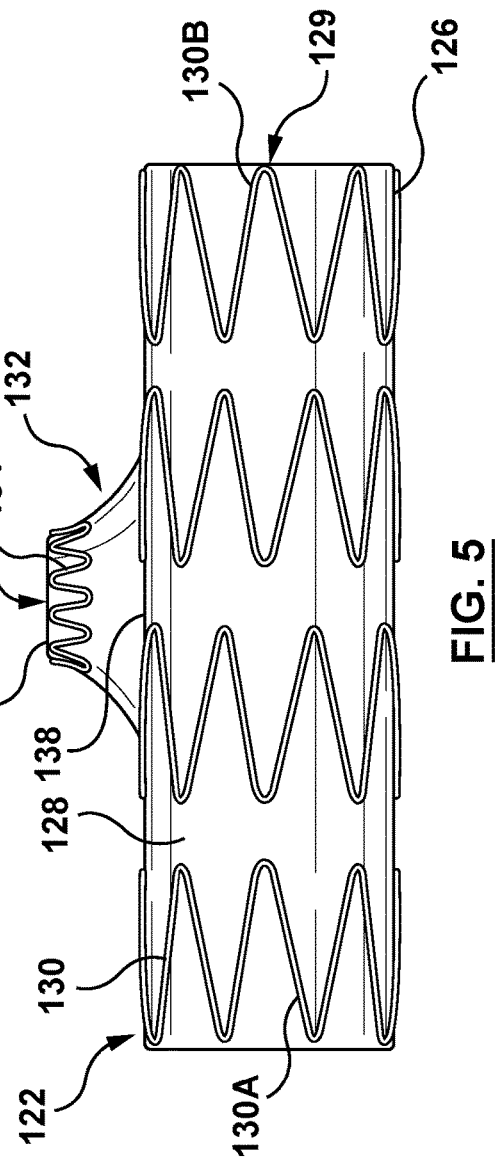
FIG. 5 is a schematic side view of a distal aortic stent-graft prosthesis, the distal aortic stent-graft prosthesis being a module or component of the aortic arch prosthetic assembly of FIG. 2, wherein the distal aortic stent-graft prosthesis is shown deployed but not in situ.

Turning now to FIG. 5, distal aortic stent-graft prosthesis 122 is configured for placement in a distal portion of the aorta arch, adjacent to the left subclavian artery and/or. Similar to proximal aortic stent-graft prosthesis 102, distal aortic stent-graft prosthesis 122 includes graft material 128 coupled to circumferential stents 130. Graft material 128 may be coupled to circumferential stents 130 using stitching or other means. In the embodiment shown in FIG. 5, circumferential stents 130 are coupled to an outside surface of graft material 128. However, circumferential stents 130 may alternatively be coupled to an inside surface of graft material 128. Although shown with four circumferential stents, it will be understood by one of ordinary skill in the art that distal aortic stent-graft prosthesis 122 may include a greater or smaller number of stents depending upon the desired length of distal aortic stent-graft prosthesis 122 and/or the intended application thereof. Graft material 128 may be any suitable graft material, for example and not limited to, woven polyester, DACRON® material, expanded polytetrafluoroethylene, polyurethane, silicone, or other suitable materials. Circumferential stents 130 may be any conventional stent material or configuration. As shown, circumferential stents 130 are preferably made from a shape memory material, such as nickel-titanium alloy (nitinol), and are formed into a zig-zag configuration. The configuration of circumferential stents 130 is merely exemplary, and circumferential stents 130 may have any suitable configuration known in the art, including but not limiting to a continuous or non-continuous helical configuration. Distal aortic stent-graft prosthesis 122 includes a proximal end 124 and a distal end 126. In an embodiment hereof, as shown in FIG. 5, both a proximal-most stent 130A and a distal-most stent 130B extend only to the edge of the graft material 128 in a closed-web configuration as shown. In another embodiment hereof, the proximal-most stent and/or distal-most stent may extend outside of the graft material 128 in an open-web or uncovered configuration. Graft material 128 has a tubular configuration and as such defines a lumen 129 therethrough. Distal aortic stent-graft prosthesis 122 further includes a coupling 132. Distal aortic stent-graft prosthesis 122 may be similar to the Medtronic, Inc.'s VALIANT MONA LSA thoracic stent-graft, or other known stent-grafts.

Coupling 132 is similar to coupling 112 in structure and is disposed on a midportion of distal aortic stent-graft prosthesis 122 corresponding to an opening in graft material 128. For sake of illustration, coupling 132 is shown approximately in the middle of distal aortic stent-graft prosthesis 122 but the location of coupling 132 may vary and coupling 132 may be disposed closer to proximal end 124 or may be disposed closer to distal end 126. In addition, for sake of illustration, coupling 132 is shown extending radially away from an outer surface of graft material 128 and thus may be considered an external coupling. However, coupling 132 may also be inverted so as to extend radially inward from an inner surface of graft material 128 and thus may be considered an internal coupling. Similar to coupling 112, coupling 132 is generally frustoconically shaped and is formed from graft material having a base 138 and a top 136. Coupling 132 has similar dimensions to coupling 112 except that since coupling 132 is configured to be used at the junction of the aorta and left common carotid artery or the junction of the aorta and left subclavian artery, the diameter of the top 136 may be approximately 6-14 mm. Similar to wireform 114, a circumferential stent or annular support wireform 134 may be coupled to the graft material of coupling 122 around top 136.

Figure 6:
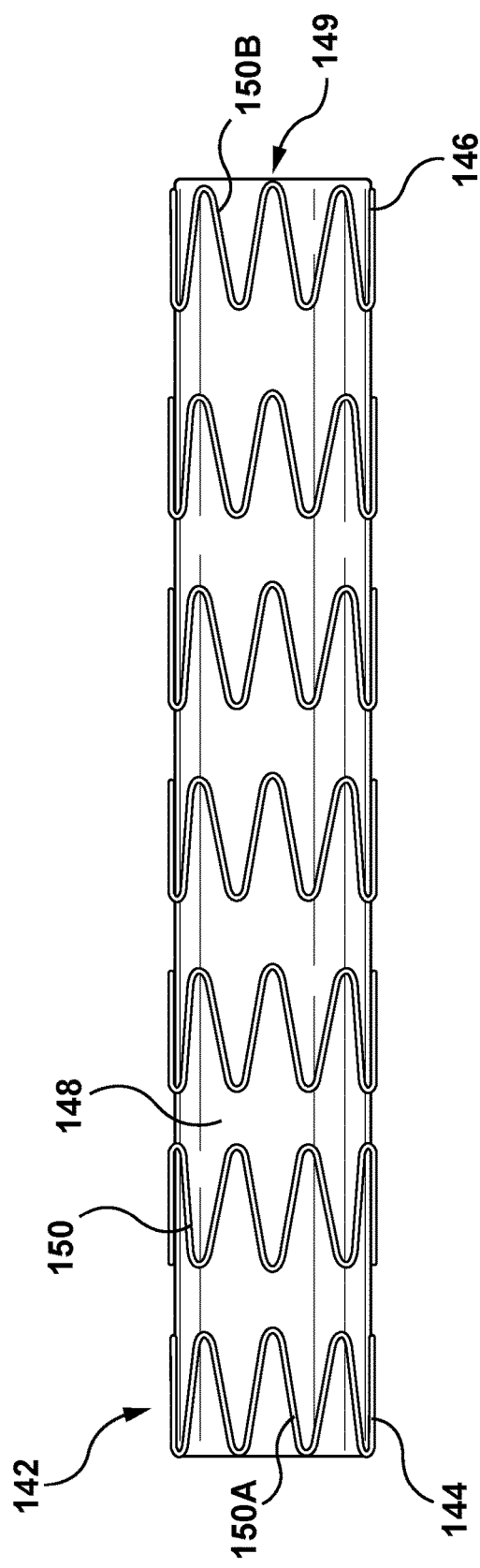
FIG. 6 is a schematic side view of a first branch stent-graft prosthesis, the first branch stent-graft prosthesis being a module or component of the aortic arch prosthetic assembly of FIG. 2, wherein the first branch stent-graft prosthesis is shown deployed but not in situ and is configured for placement within the brachiocephalic artery.

Turning now to FIG. 6, first branch stent-graft prosthesis 142 is configured for placement in a vessel such as the brachiocephalic artery. First branch stent-graft prosthesis 142 includes graft material 148 coupled to circumferential stents 150. Graft material 148 may be coupled to circumferential stents 150 using stitching or other means. In the embodiment shown in FIG. 6, circumferential stents 150 are coupled to an outside surface of graft material 148. However, circumferential stents 150 may alternatively be coupled to an inside surface of graft material 148. Although shown with seven circumferential stents, it will be understood by one of ordinary skill in the art that first branch stent-graft prosthesis 142 may include a greater or smaller number of stents depending upon the desired length of first branch stent-graft prosthesis 142 and/or the intended application thereof. Graft material 148 may be any suitable graft material, for example and not limited to, woven polyester, DACRON® material, expanded polytetrafluoroethylene, polyurethane, silicone, or other suitable materials. Circumferential stents 150 may be any conventional stent material or configuration. As shown, circumferential stents 150 are preferably made from a shape memory material, such as nickel-titanium alloy (nitinol), and are formed into a zig-zag configuration. The configuration of circumferential stents 150 is merely exemplary, and circumferential stents 150 may have any suitable configuration known in the art, including but not limiting to a continuous or non-continuous helical configuration. First branch stent-graft prosthesis 142 includes a proximal end 144 and a distal end 146. In an embodiment hereof, as shown in FIG. 6, both a proximal-most stent 150A and a distal-most stent 150B extend only to the edge of the graft material 148 in a closed-web configuration as shown. In another embodiment hereof, the proximal-most stent and/or distal-most stent may extend outside of the graft material 148 in an open-web or uncovered configuration. Graft material 148 has a tubular configuration and as such defines a lumen 149 therethrough. First branch stent-graft prosthesis 142 may be similar to the Medtronic, Inc.'s VALIANT® thoracic stent-graft, or other known stent-grafts.

First branch stent-graft prosthesis 142 is configured to exert a higher radial force than the radial force of proximal aortic stent-graft prosthesis 102 and/or distal aortic stent-graft prosthesis 122. As used herein, "radial force" includes both a radial force exerted during expansion/deployment as well as a chronic radial force continuously exerted after implantation such that a scaffold has a predetermined compliance or resistance as the surrounding native anatomy, i.e., the ascending aorta or the native valve annulus, expands and contracts during the cardiac cycle. The radial force of proximal aortic stent-graft prosthesis 102 and/or distal aortic stent-graft prosthesis 122 is configured to be lower than that of first branch stent-graft prosthesis 132 in order to avoid collapse of first branch stent-graft prosthesis 142 when proximal aortic stent-graft prosthesis 102 and/or distal aortic stent-graft prosthesis 122 are deployed against and adjacent thereof and thus maintain perfusion of the brachiocephalic artery. In order to configure the stent-graft prostheses with differing relative radial forces, stents 150 of first branch stent-graft prosthesis 142 may be constructed with relatively thicker and/or shorter segments of material than stents 130 of distal aortic stent-graft prosthesis 122 and/or stents 110 of proximal aortic stent-graft prosthesis 102. Conversely, stents 110, 130 of proximal aortic stent-graft prosthesis 102 and/or distal aortic stent-graft prosthesis 122, respectively, may be constructed with relatively thinner and/or longer segments of material than stents 150 of first branch stent-graft prosthesis 142. Shorter and/or thicker scaffold segments have less flexibility but greater radial force to ensure that stents 110, 130 of proximal aortic stent-graft prosthesis 102 and distal aortic stent-graft prosthesis 122, respectively, do not collapse lumen 140 of first branch stent-graft prosthesis 142. Other variations or modification of the stents/scaffolds may be used to configure the stents/scaffolds with differing relative radial forces without departing from the scope of the present invention.

Figure 7:
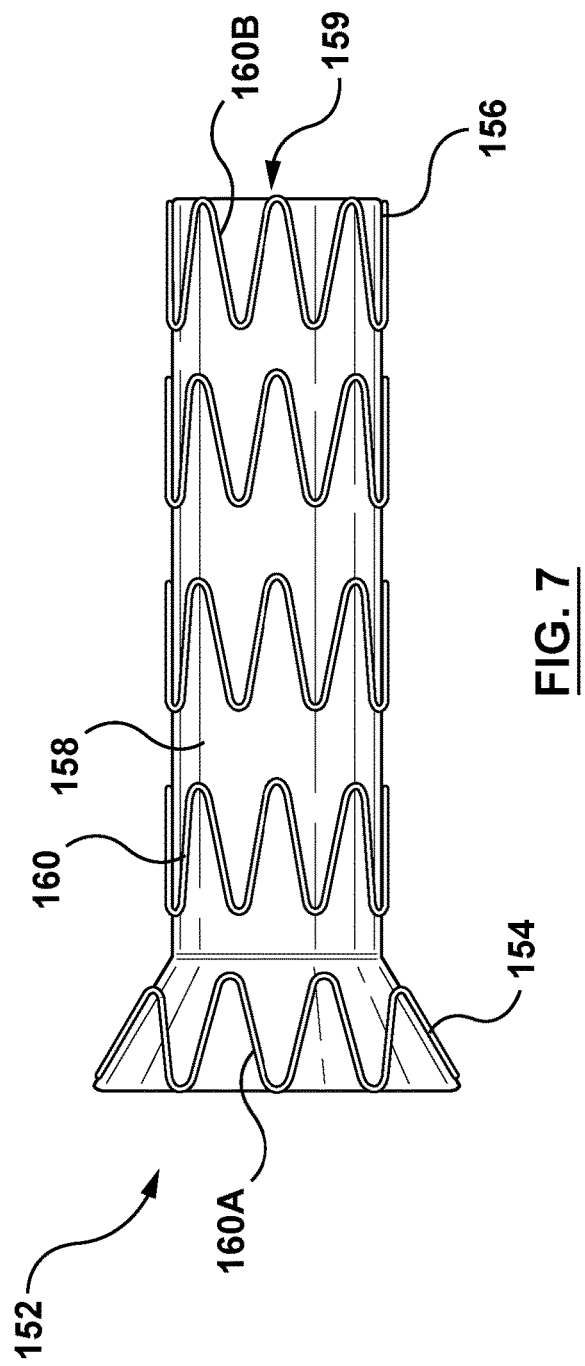
FIG. 7 is a schematic side view of a second branch stent-graft prosthesis, the second branch stent-graft prosthesis being a module or component of the aortic arch prosthetic assembly of FIG. 2, wherein the second branch stent-graft prosthesis is shown deployed but not in situ and is configured for placement within the left common carotid artery or the left subclavian artery.
Figure 11:
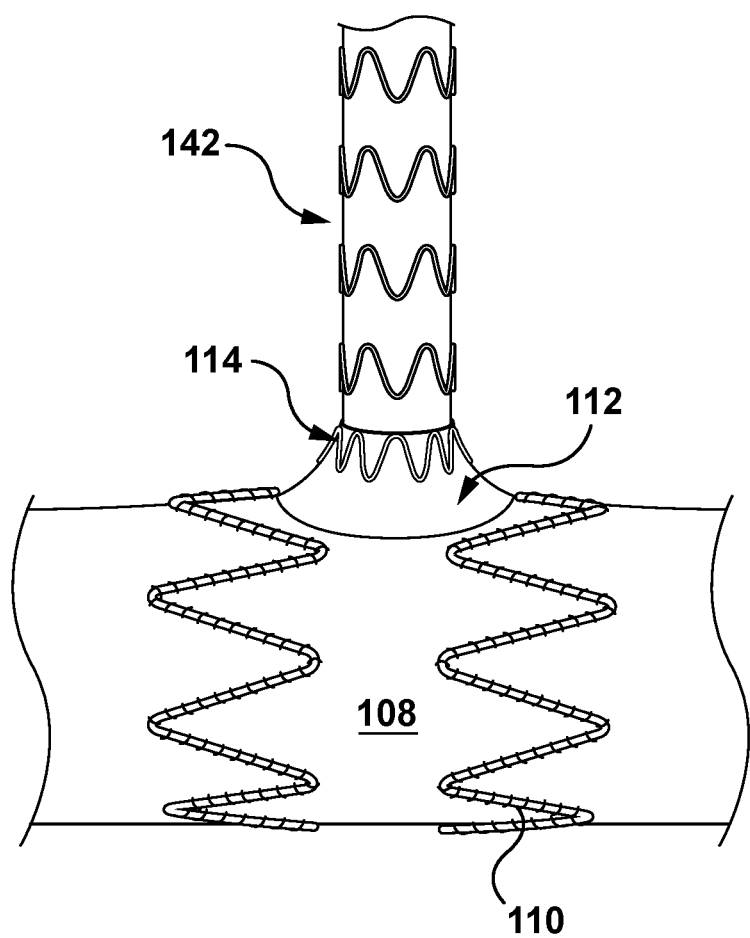
FIG. 11 is a schematic illustration of the coupling of FIG. 8 having a branch stent-graft prosthesis deployed therein.

With reference to FIG. 7, second branch stent-graft prosthesis 152 is configured for placement in a vessel such as the left common carotid artery or the left subclavian artery. Second branch stent-graft prosthesis 152 includes graft material 158 coupled to circumferential stents 160. Graft material 158 may be coupled to circumferential stents 160 using stitching or other means. In the embodiment shown in FIG. 7, circumferential stents 160 are coupled to an outside surface of graft material 158. However, circumferential stents 160 may alternatively be coupled to an inside surface of graft material 158. Although shown with five circumferential stents, it will be understood by one of ordinary skill in the art that second branch stent-graft prosthesis 152 may include a greater or smaller number of stents depending upon the desired length of second branch stent-graft prosthesis 152 and/or the intended application thereof. Graft material 158 may be any suitable graft material, for example and not limited to, woven polyester, DACRON® material, expanded polytetrafluoroethylene, polyurethane, silicone, or other suitable materials. Circumferential stents 160 may be any conventional stent material or configuration. As shown, circumferential stents 160 are preferably made from a shape memory material, such as nickel-titanium alloy (nitinol), and are formed into a zig-zag configuration. The configuration of circumferential stents 160 is merely exemplary, and circumferential stents 160 may have any suitable configuration known in the art, including but not limiting to a continuous or non-continuous helical configuration. Second branch stent-graft prosthesis 152 includes a proximal end 154 and a distal end 156. In an embodiment hereof, as shown in FIG. 7, both a proximal-most stent 160A and a distal-most stent 160B extend only to the edge of the graft material 158 in a closed-web configuration as shown. In another embodiment hereof, the proximal-most stent and/or distal-most stent may extend outside of the graft material 158 in an open-web or uncovered configuration. Further, as shown in FIG. 7, in an embodiment hereof proximal end 154 of second branch stent-graft prosthesis 152 is flared. The flared proximal end 154 aids in sealing of second branch stent-graft prosthesis 152 by matching the flare thereof with the taper of the outer surface of coupling 132 of distal aortic stent-graft prosthesis 122. Graft material 158 has a tubular configuration and as such defines a lumen 159 therethrough. Second branch stent-graft prosthesis 152 may be similar to the Medtronic, Inc.'s VALIANT® thoracic stent-graft, or other known stent-grafts.

Although not shown, in another embodiment hereof, proximal end 144 of first branch stent-graft prosthesis 142 may also be flared similar to proximal end 154 of second branch stent-graft prosthesis 152 to aid in sealing between first branch stent-graft prosthesis 142 and coupling 112 of proximal aortic stent-graft prosthesis 102.

As will be explained in more detail herein, first and second branch stent-graft prostheses 142, 152 are delivered and deployed through couplings 112, 132 of proximal and distal aortic stent-graft prostheses 102, 122, respectively. After implantation, pulsatile expansion and/or other movement of the branch vessel may occur during the cardiac cycle. Such movement of the branch vessel may eventually degrade the seal between couplings 112, 132 of proximal and distal aortic stent-graft prostheses 102, 122, respectively, due to deformation of the material of the branch vessel prosthesis. More particularly, referring now to FIG. 11, a schematic illustration of coupling 112 including support wireform 114 with first branch stent-graft prosthesis 142 deployed therein is shown. Support wireform 114 produces an interference seal between first branch stent-graft prosthesis 142 and coupling 112. Support wireform 114 enhances sealing between first branch stent-graft prosthesis 142 and coupling 112 because first branch stent-graft prosthesis 142 expands or deploys within coupling 112 to abut against support wireform 114, the result being that support wireform 114 securely fits around a proximal portion of first branch stent-graft prosthesis 142.

In one embodiment, the deployed diameter of support wireform 114 may be undersized or smaller than the deployed diameter of first branch stent-graft prosthesis 142 to provide a more effective seal between coupling 112 and first branch stent-graft prosthesis 142. More particularly, the deployed diameter of support wireform 114 may be up to approximately 30% smaller than the deployed diameter of first branch stent-graft prosthesis 142. Deployment of first branch stent-graft prosthesis 142 into coupling 112 results in expansion of branch prosthesis 142 to the limiting diameter of support wireform 114. Thus, even if movement of first branch stent-graft prosthesis 142 occurs after implantation, the shape memory of undersized support wireform 114 urges coupling 112 to the shape memory diameter of support wireform 114 to thereby compensate for the movement and retain the seal between coupling 112 and first branch stent-graft prosthesis 142. Undersized support wireform 114 and first branch stent-graft prosthesis 142 are two elastic pieces exerting opposing forces onto each other. In other words, because branch prosthesis 142 wants to expand to a larger diameter than the limiting diameter of support wireform 114, branch prosthesis 142 provides an outward force and support wireform 114 provides a counteracting inward force to maintain the seal between coupling 112 and branch prosthesis 142.

In the embodiment of FIGS. 6 and 7, the scaffolding or support structure of first and second branch stent-graft prostheses 142, 152 has been illustrated as a series of independent or separate self-expanding stents/sinusoidal patterned rings. However, as will be understood by one of ordinary skill in the art, the support structure or scaffolding of first and second branch stent-graft prostheses 142, 152 may have other configurations such as a series of sinusoidal patterned rings coupled to each other to form a self-expanding stent or a unitary tubular radially-compressible scaffold.

U.S. Patent Pub. No. 20120271401 to Bruszewski et al., assigned to the same assignee as the present disclosure, previously incorporated by reference herein, describes one or more examples of a delivery system that can be used to deliver each module of aortic arch prosthetic assembly 100 to the target location within a vessel and many other delivery systems known to those skilled in the art could be utilized. For example, each module of aortic arch prosthetic assembly 100 could be mounted onto a balloon to be expanded when at the target site. Thus, stated another way, one or more modules may be balloon-expandable rather than self-expanding. Further, it may be desirable to utilize a combination of balloon-expandable modules and self-expanding modules. Other stent-graft-delivery systems, for example and not by way of limitation, the delivery systems described in U.S. Published Patent Application Publication Nos. 2008/0114442 and 2008/0262590 and U.S. Pat. No. 7,264,632, and U.S. patent application Ser. Nos. 12/425,616 and 12/842,628, each filed Apr. 17, 2009, each of which is incorporated herein by reference in its entirety, may be utilized to deliver and deploy each module of aortic arch prosthetic assembly 100.

FIGS. 12-23 schematically show a method of delivering and deploying aortic arch prosthetic assembly 100 within the aortic arch. In the example described herein, the aortic arch prosthetic assembly 100 is delivered and deployed into the aortic arch. Portions of the aorta include the ascending aorta, the aortic arch (labeled as "AA" in the figures), and the descending aorta. Branching from the aortic arch are the brachiocephalic artery BCA, the left common carotid LCC artery, and the left subclavian artery LSA. An aneurysm (not shown) may form in any area of the aortic arch, and can be difficult to bypass or exclude with a single stent-graft because blood flow to the branch arteries must be maintained. As previously stated, although the description of embodiments hereof is primarily in the context of modular devices for treating aneurysm disease within an aortic arch, the modular devices described herein can also be used to treat other aortic arch pathologies including but not limited to dissections, penetrating ulcers, intramural hematomas, transections, and pseudoaneurysms.

Prior to the procedure for inserting aortic arch prosthetic assembly 100, a surgical by-pass procedure installing bypass 162 is performed to connect the left common carotid LCC artery to the left subclavian artery LSA. Such surgical bypass procedures may be performed one to two weeks prior to insertion of aortic arch prosthetic assembly 100, or may be performed at the same time as the implantation procedure for aortic arch prosthetic assembly 100, and present significantly less complications and risk than a surgical solution to repair an aneurysm in the aortic arch. In this manner, maintaining perfusion to one of the left subclavian artery LSA or the left common carotid LCC artery will simultaneously maintain perfusion to the other branch artery.

Figure 12:
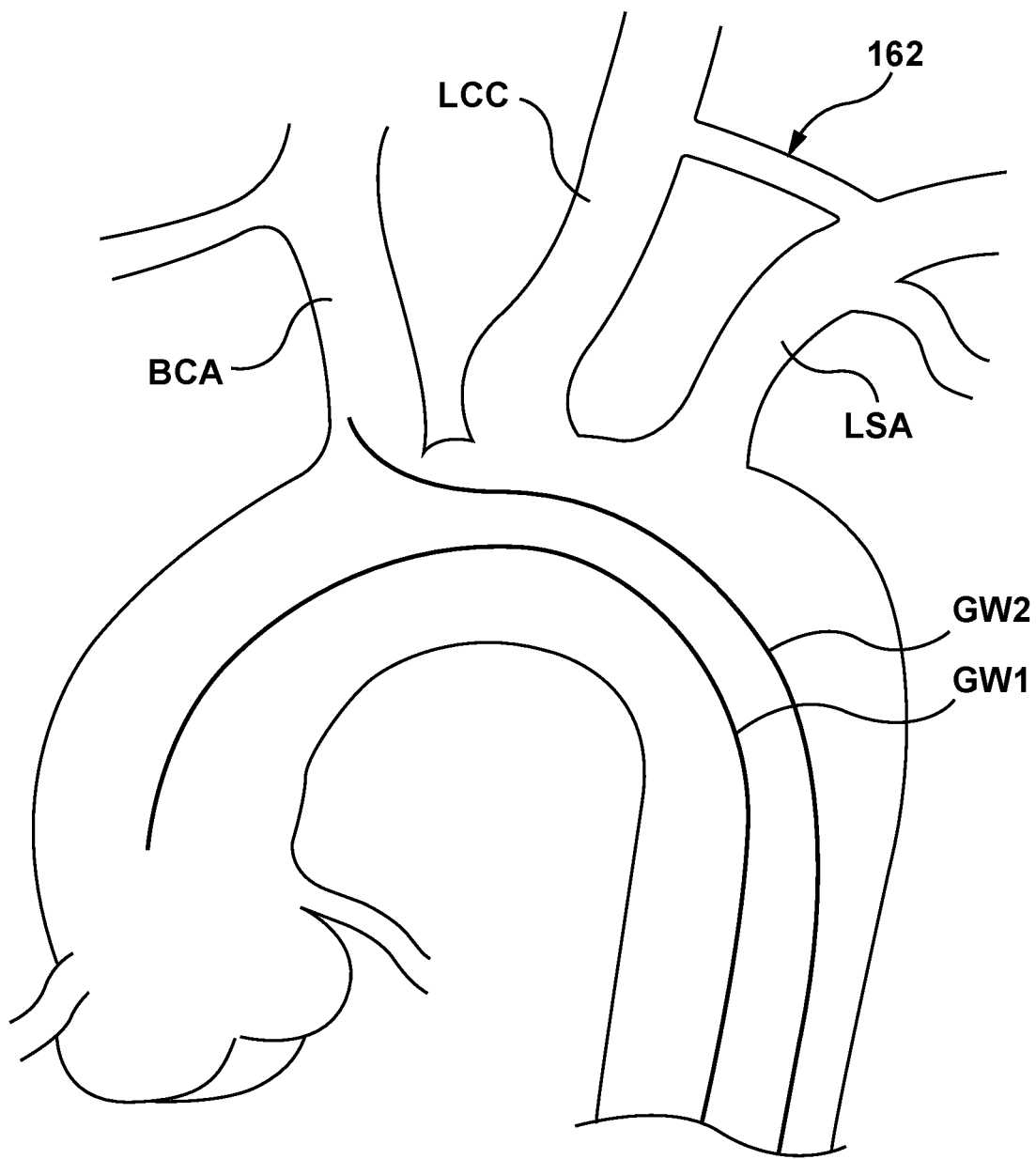
FIGS. 12-23 are schematic illustrations of progressive steps of a method for delivering and deploying the aortic arch prosthetic assembly of FIG. 2.

FIG. 12 shows a first guidewire GW1 and a second guidewire GW2 advanced through the descending aorta, through the aortic arch, and into the ascending aorta. Guidewires GW1, GW2 are typically inserted into the femoral artery and routed up through the abdominal aorta, and into the thoracic aorta, as is known in the art. In another embodiment hereof (not shown), guidewires GW1, GW2 can be introduced via supra aortic or transapical access.

Figure 13:
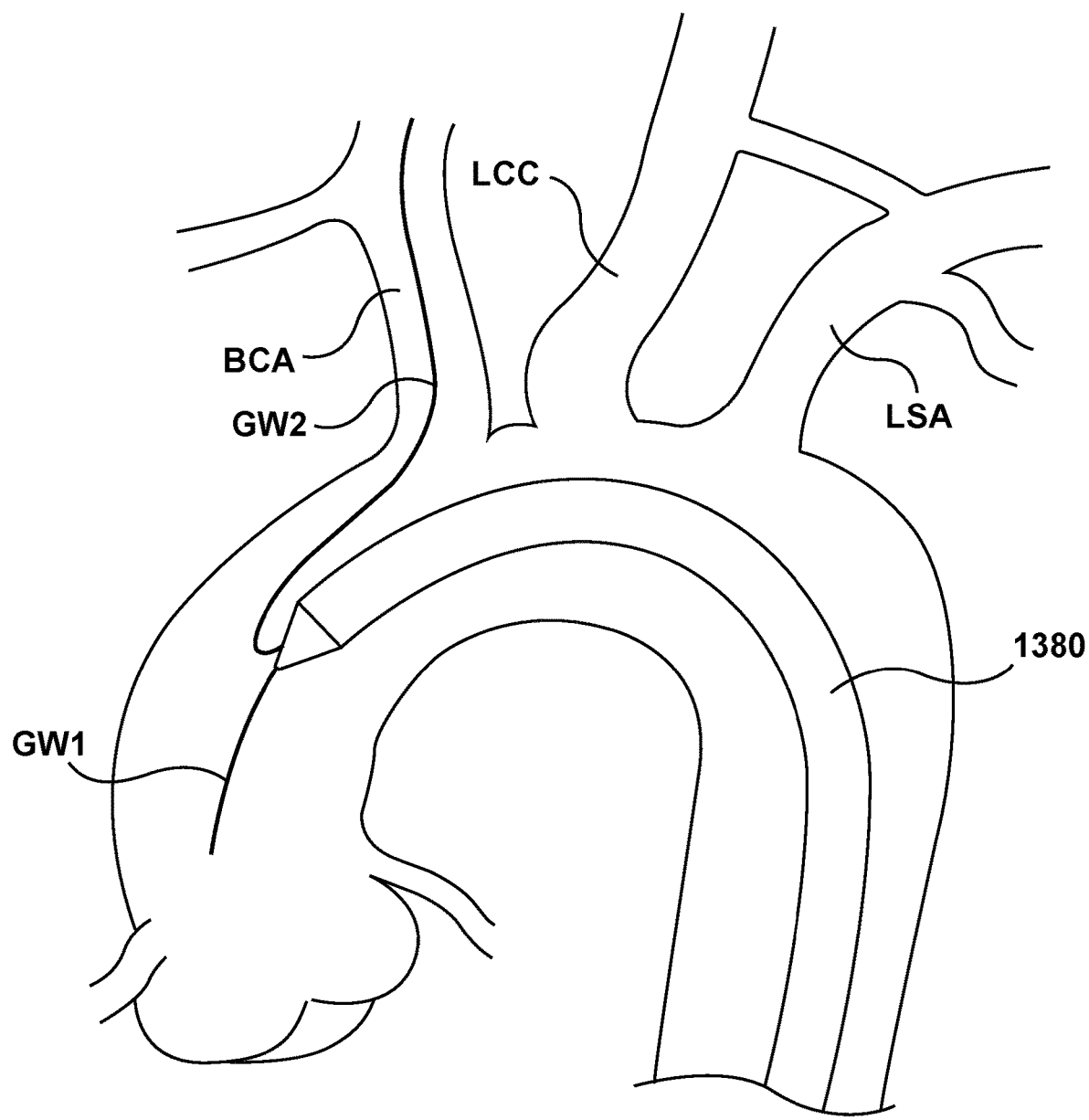

FIG. 13 shows a stent-graft delivery system 1380, with proximal aortic stent-graft prosthesis 102 compressed therein, advanced over guidewires GW1, GW2 to the target location in the aortic arch. The location of the stent-graft delivery system 1380 and/or the proximal aortic stent-graft prosthesis 102 may be verified radiographically and delivery system 1380 and/or proximal aortic stent-graft prosthesis 102 may include radiopaque markers as known in the art. Second guidewire GW2 may also be locked at its distal or superaortic end so as to prevent second guidewire GW2 from retracting. More particularly, the distal end of second guidewire GW2 may be captured with a snare (not shown) and pulled through the brachiocephalic artery BCA as shown in FIG. 13. The distal end of second guidewire GW2 is pulled until second guidewire GW2 extends from a brachial entry point through the aorta and out at the femoral arteriotomy site, as is known to those of ordinary skill in the art as a through-and-through wire technique. The through-and-through access improves the ability to stabilize and manipulate second guidewire GW2 during the procedure in addition, the through-and-through wire technique reduces the complexity of branch stent-graft deployment to the branch vessels in the case of axial or rotational misalignment or patient specific anatomical variation.

Figure 14:
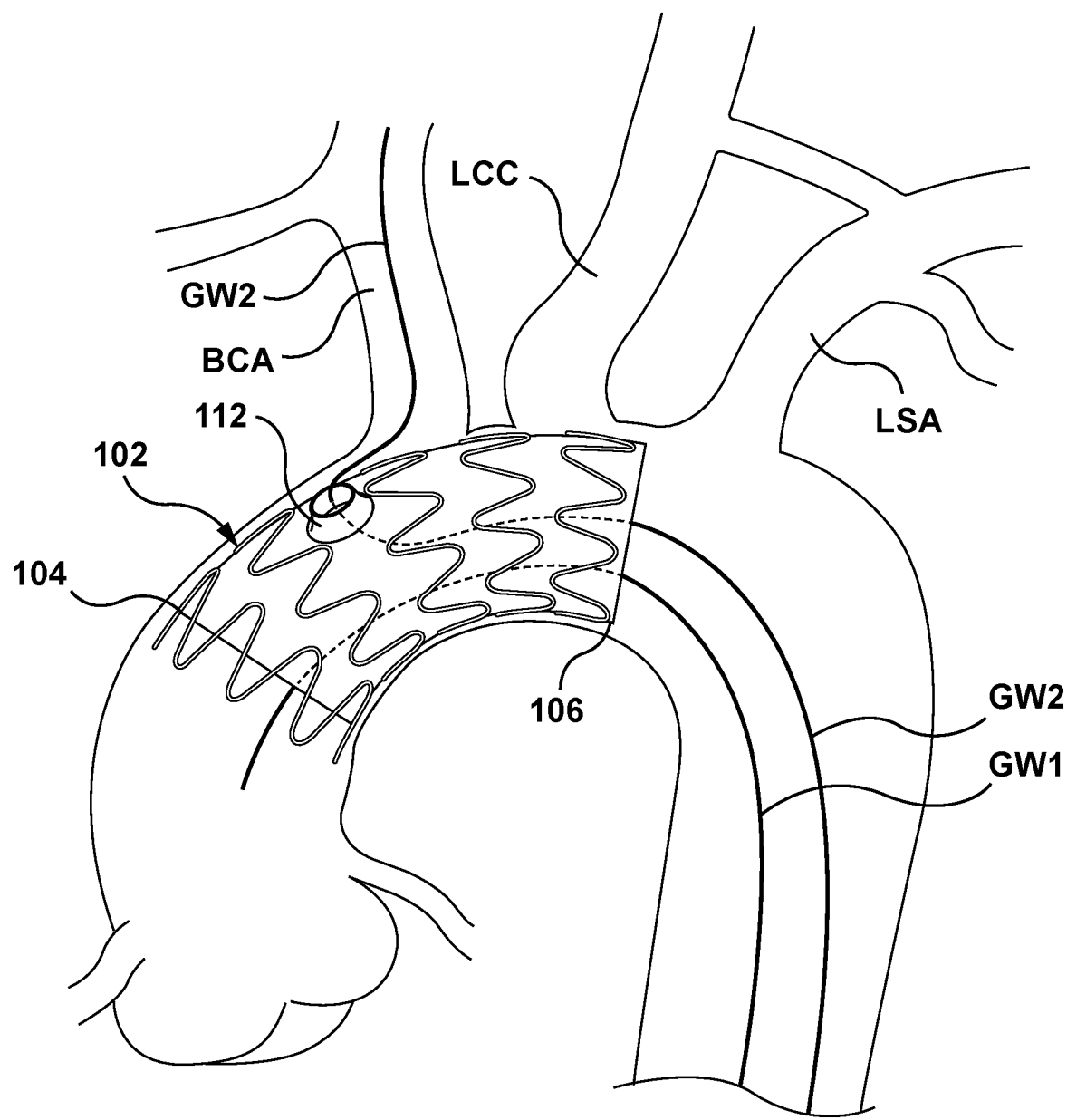

After stent-graft delivery system 1380 is in the location where the coupling 112 of proximal aortic stent-graft prosthesis 102 is disposed proximal to the opening into the brachiocephalic artery BCA (i.e., the ostium of the brachiocephalic artery BCA), an outer sleeve or sheath of stent-graft delivery system 1380 is retracted proximally to deploy proximal aortic stent-graft prosthesis 102. FIG. 14 illustrates proximal aortic stent-graft prosthesis 102 deployed within the aorta, with coupling 112 disposed proximal to the ostium of the brachiocephalic artery BCA. More particularly, the outer sleeve or sheath of stent-graft delivery system 1380 may initially be retracted proximally to a position adjacent to coupling 112 to initially only release coupling 112. When coupling 112 extends radially away from an outer surface of graft material 108 as an external coupling, coupling 112 including support wireform 114 provides structural integrity to the top of coupling 112, and orients the distal end of the coupling radially outwards or towards the vessel wall of the aorta. Once coupling 112 is deployed, the outer sleeve or sheath of stent-graft delivery system 1380 may be further retracted to deploy the remaining length of proximal aortic stent-graft prosthesis 102. Once coupling 112 and proximal aortic stent-graft prosthesis 102 are deployed, delivery system 1380 may be removed leaving proximal aortic stent-graft prosthesis 102 deployed in situ as shown in FIG. 14 with first and second guidewires GW1, GW2 disposed therethrough. In this embodiment, first guidewire GW1 is left in place for subsequent delivery of distal aortic stent-graft prosthesis 122 thereover to minimize the number of manipulations but in another embodiment hereof first guidewire GW1 may be removed and a different guidewire may be positioned for delivery of distal aortic stent-graft prosthesis 122.

Figure 15:
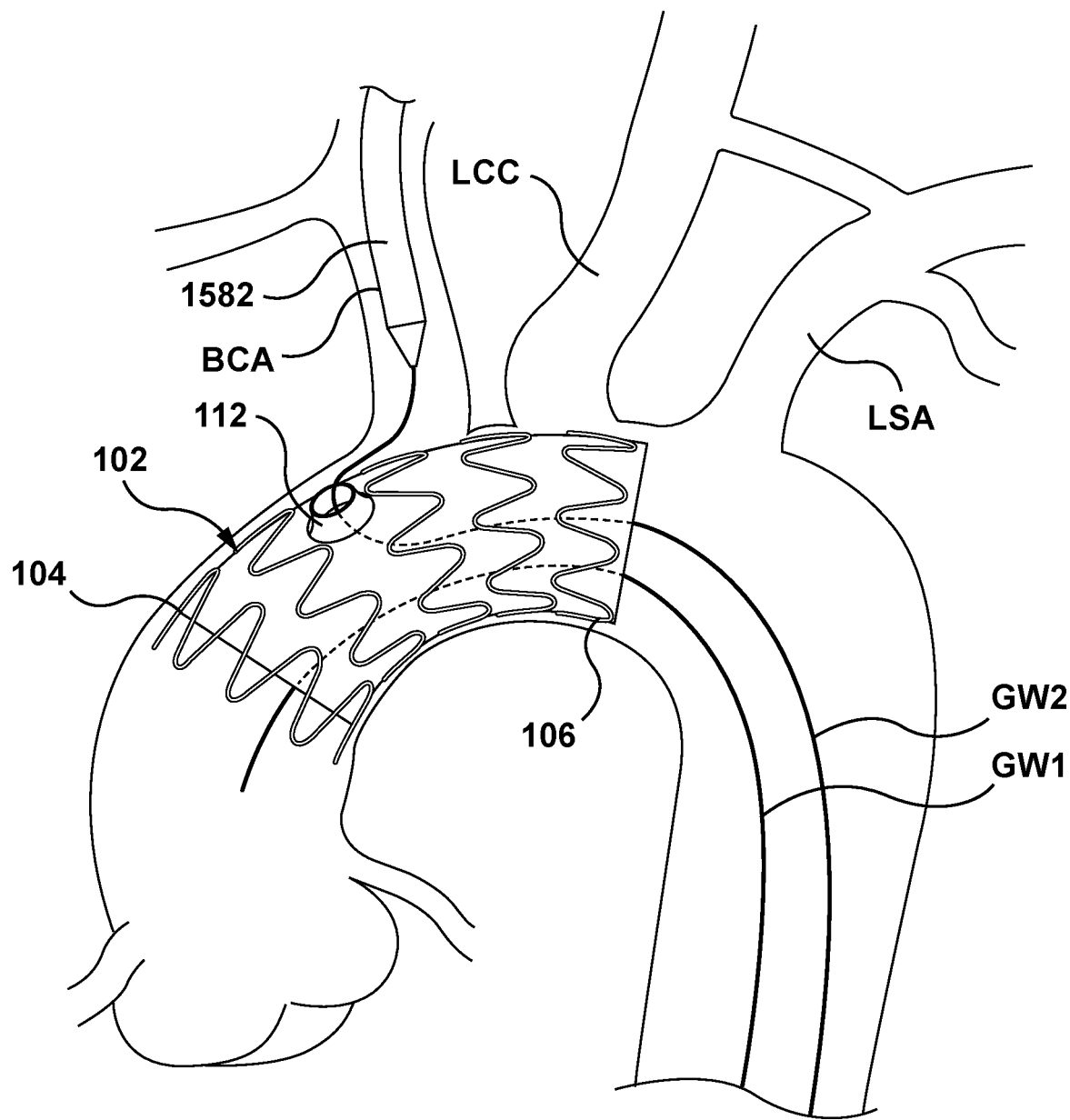
Figure 16:
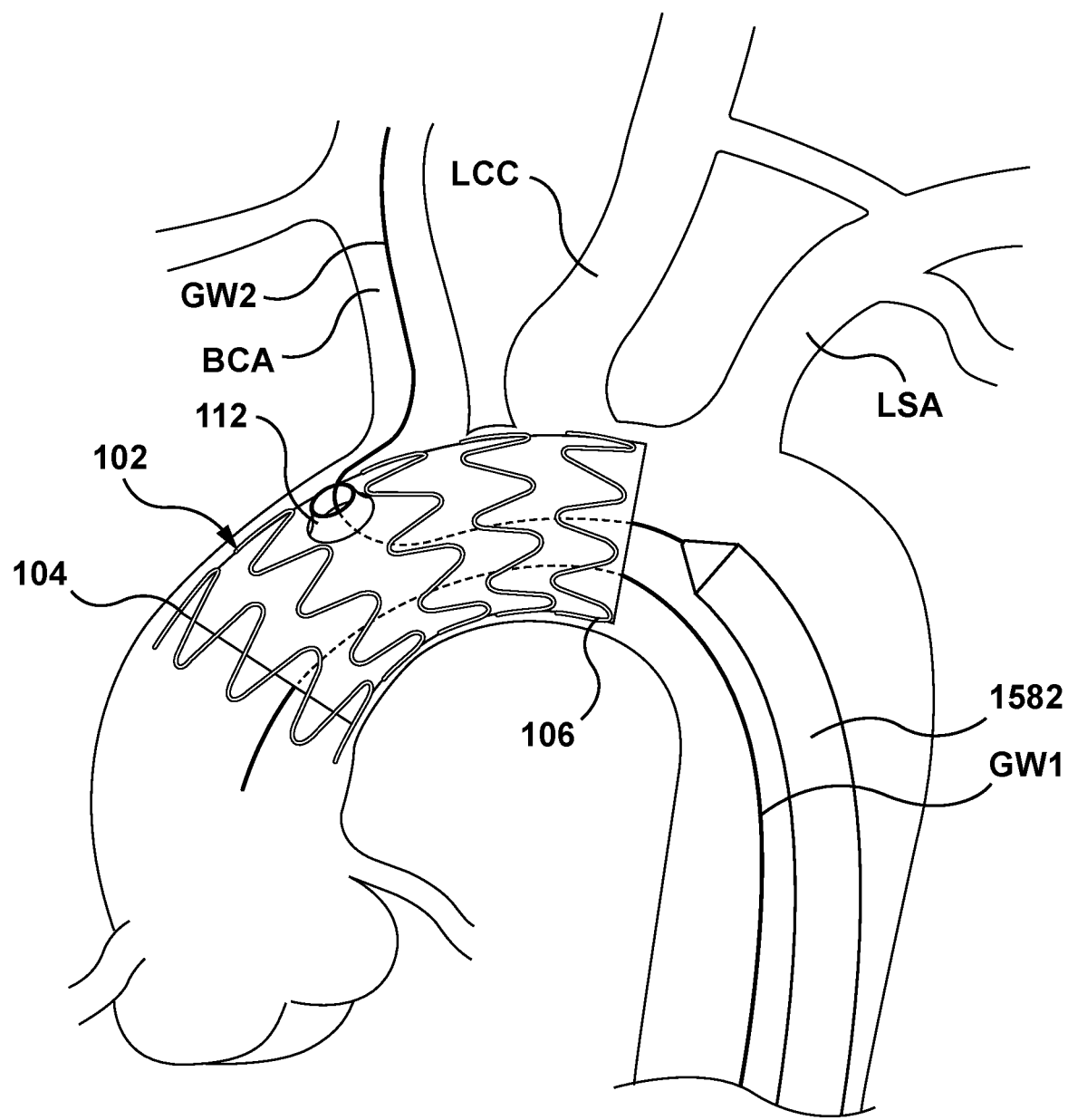

FIG. 15 shows a branch stent-graft delivery system 1582, with first branch stent-graft prosthesis 142 compressed therein, advanced over second guidewire GW2 to the target location in the brachiocephalic artery BCA and the ascending aorta. The location of the branch stent-graft delivery system 1582 and/or the first branch stent-graft prosthesis 142 compressed therein may be verified radiographically and delivery system 1582 and/or first branch stent-graft prosthesis 142 may include radiopaque markers as known in the art. Branch stent-graft delivery system 1582 may be conventional and contains first branch stent-graft prosthesis 142 therein. In the embodiment of FIG. 15, branch stent-graft delivery system 1582 is advanced into the brachiocephalic artery BCA via the brachial entry point of second guidewire GW2. In another embodiment hereof depicted in FIG. 16, branch stent-graft delivery system 1582 with first branch stent-graft prosthesis 142 compressed therein is delivered into the brachiocephalic artery BCA via the femoral entry point of second guidewire GW2.

Figure 17:
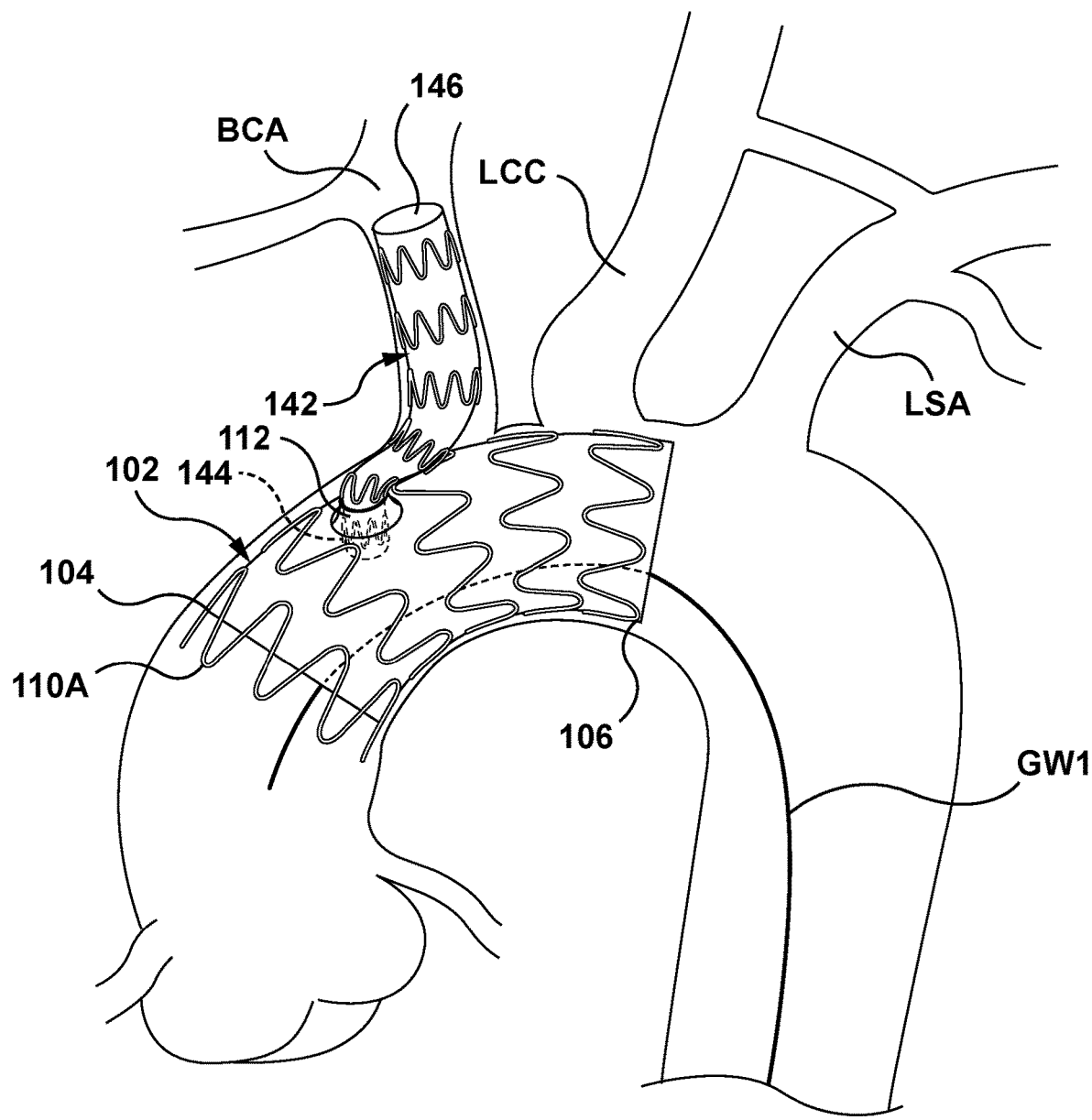

Regardless of which entry point of second guidewire GW2 is utilized, first branch stent-graft prosthesis 142 is advanced over second guidewire GW2 until it is positioned within the brachiocephalic artery BCA as desired with proximal end 144 of first branch stent-graft prosthesis 142 internal to proximal aortic stent-graft prosthesis 102. Once first branch stent-graft prosthesis 142 is positioned as desired, an outer sheath of branch stent-graft delivery system 1582 constraining first branch stent-graft prosthesis 142 is then retracted proximally, thereby releasing first branch stent-graft prosthesis 142 from the delivery system. Branch stent-graft delivery system 1582 is then removed leaving first branch stent-graft prosthesis 142 deployed in situ as shown in FIG. 17. As shown in FIG. 17, second guidewire GW2 may also be removed at this point in the method while first guidewire GW1 still remains in place for subsequent delivery of distal aortic stent-graft prosthesis 122 thereover. When deployed, first branch stent-graft prosthesis 142 extends within the brachiocephalic artery BCA and through coupling 112 such that proximal end 144 of first branch stent-graft prosthesis 142 is disposed internal to proximal aortic stent-graft prosthesis 102. Between the ostium/opening of the brachiocephalic artery BCA and coupling 112, first branch stent-graft prosthesis 142 extends within the aorta and is external to proximal aortic stent-graft prosthesis 102. Stated another way, a portion of first branch stent-graft prosthesis 142 is disposed outside of proximal aortic stent-graft prosthesis 102 and is sandwiched between and contacts both the outer surface of proximal aortic stent-graft prosthesis 102 and the wall of the aorta. If the aorta is aneurysmal, then first branch stent-graft prosthesis 142 may not be opposed against the outer surface of proximal aortic stent-graft prosthesis 102 and the wall of the aorta. Proximal end 144 of first branch stent-graft prosthesis 142 extends through coupling 112 and may be disposed within the lumen of proximal aortic stent-graft prosthesis 102. In an embodiment hereof, approximately 10 mm of first branch stent-graft prosthesis 142 extends within the lumen of proximal aortic stent-graft prosthesis 102. As shown on FIG. 17, proximal end 144 of first branch stent-graft prosthesis 142 does not extend to or reach the proximal-most stent 110A of proximal aortic stent-graft prosthesis 102. Stated another way, the proximal-most stent 110A of proximal aortic stent-graft prosthesis 102 is positioned proximal of the proximal end 144 of first branch stent-graft prosthesis 142. First branch stent-graft prosthesis 142 proximally reroutes or displaces the ostium of the brachiocephalic artery BCA which is now defined by proximal end 144 of first branch stent-graft prosthesis 142 to the ascending aorta.

With a portion of first branch stent-graft prosthesis 142 being disposed outside of or external to proximal aortic stent-graft prosthesis 102, proximal aortic stent-graft prosthesis 102 contacts or abuts against an outer surface of deployed first branch stent-graft prosthesis 142. However, since first branch stent-graft prosthesis 142 has a higher radial force than proximal aortic stent-graft prosthesis 102 as described herein, proximal aortic stent-graft prosthesis 102 does not collapse or otherwise interfere with deployed first branch stent-graft prosthesis 142 and perfusion of the brachiocephalic artery BCA provided thereby. Proximal aortic stent-graft prosthesis 102 may be partially collapsed by deployed first branch stent-graft prosthesis 142, but lumen 109 remains at least partially open for blood to flow through proximal aortic stent-graft prosthesis 102 due to the relatively smaller size of deployed first branch stent-graft prosthesis 142.

Figure 18:
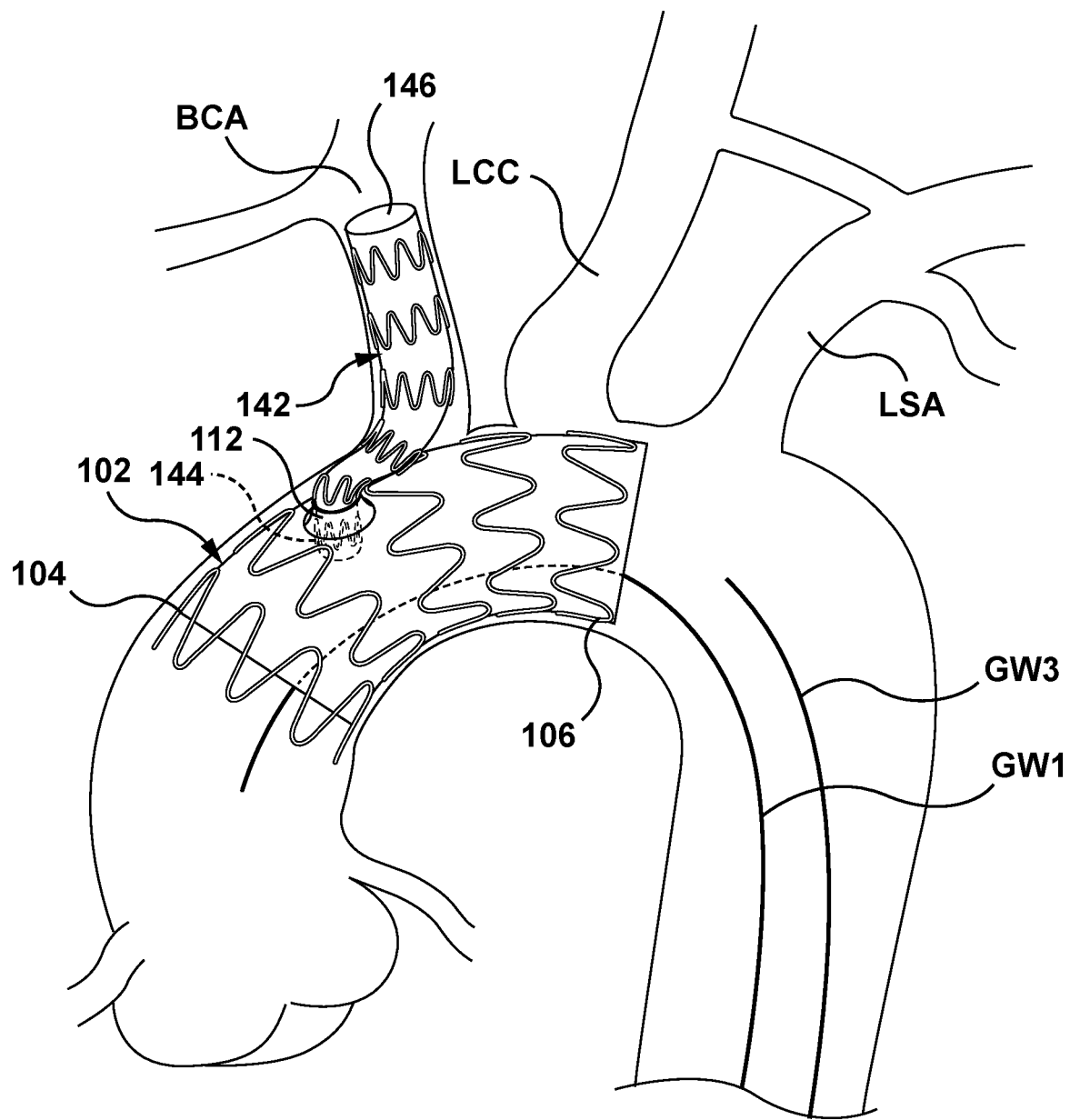

FIG. 18 shows a third guidewire GW3 advanced through the descending aorta, and into the aortic arch. Third guidewires GW3 is typically inserted into the femoral artery and routed up through the abdominal aorta, and into the thoracic aorta, as is known in the art. In another embodiment hereof (not shown), second guidewire GW2 may not be previously removed but rather may be repositioned as third guidewire GW3.

Figure 19:
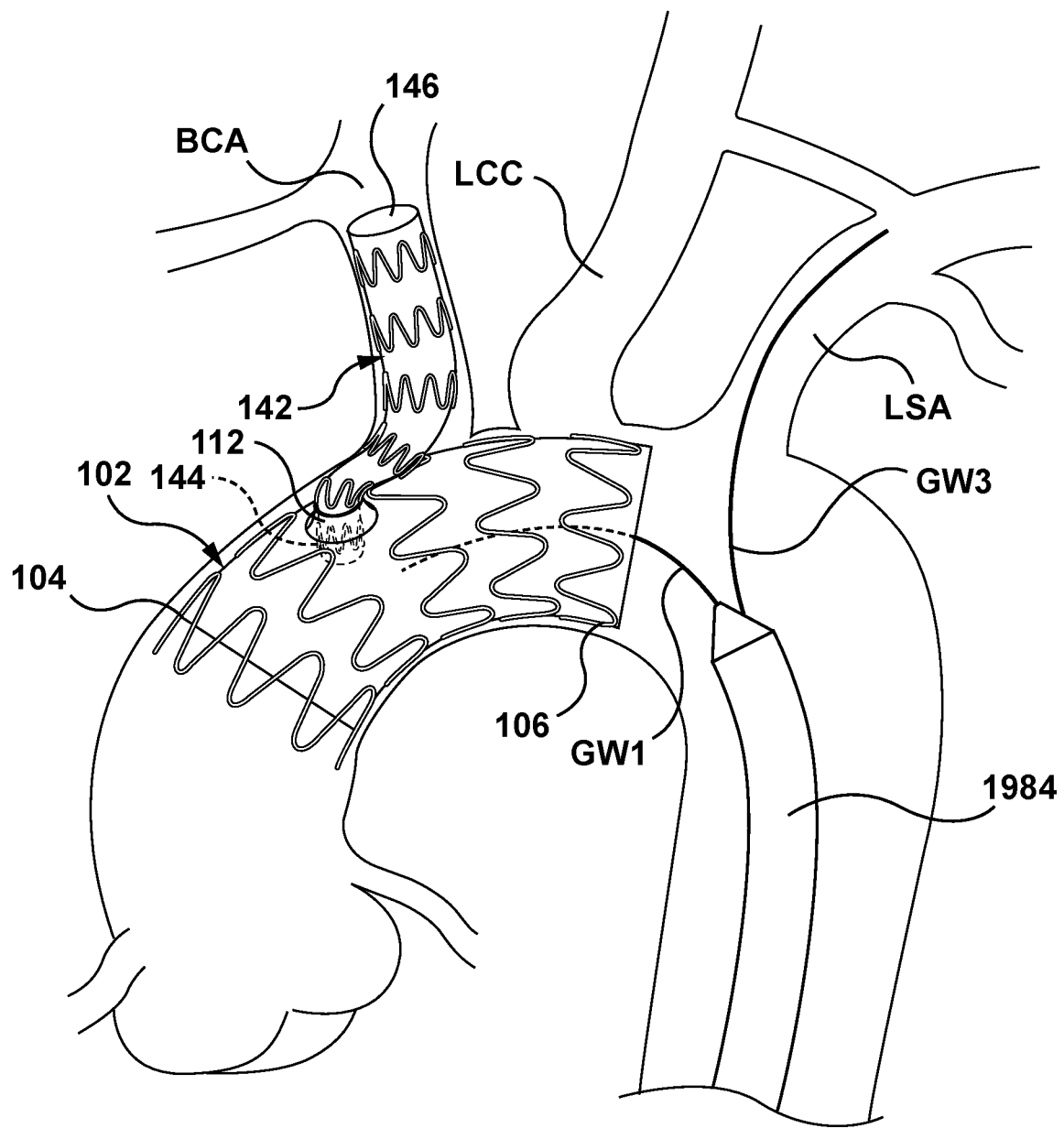

FIG. 19 shows a stent-graft delivery system 1984, with distal aortic stent-graft prosthesis 122 compressed therein, advanced over first and third guidewires GW1, GW3 to the target location in the aortic arch. The location of stent-graft delivery system 1984 and/or distal aortic stent-graft prosthesis 122 may be verified radiographically and delivery system 1984 and/or distal aortic stent-graft prosthesis 122 may include radiopaque markers as known in the art. Third guidewire GW3 may also be locked at its distal or super-aortic end so as to prevent third guidewire GW3 from retracting. More particularly, the distal end of third guidewire GW3 may be captured with a snare (not shown) and pulled through the left subclavian artery LSA as shown in FIG. 19. The distal end of third guidewire GW3 is pulled until third guidewire GW3 extends from a radial artery entry point through the aorta and out at the femoral arteriotomy site, as is known to those of ordinary skill in the art as a through-and-through wire technique. The through-and-through access improves the ability to stabilize and manipulate third guidewire GW3 during the procedure. In addition, the through-and-through wire technique reduces the complexity of branch stent-graft deployment to the branch vessels in the case of axial or rotational misalignment or patient specific anatomical variation.

Figure 20:
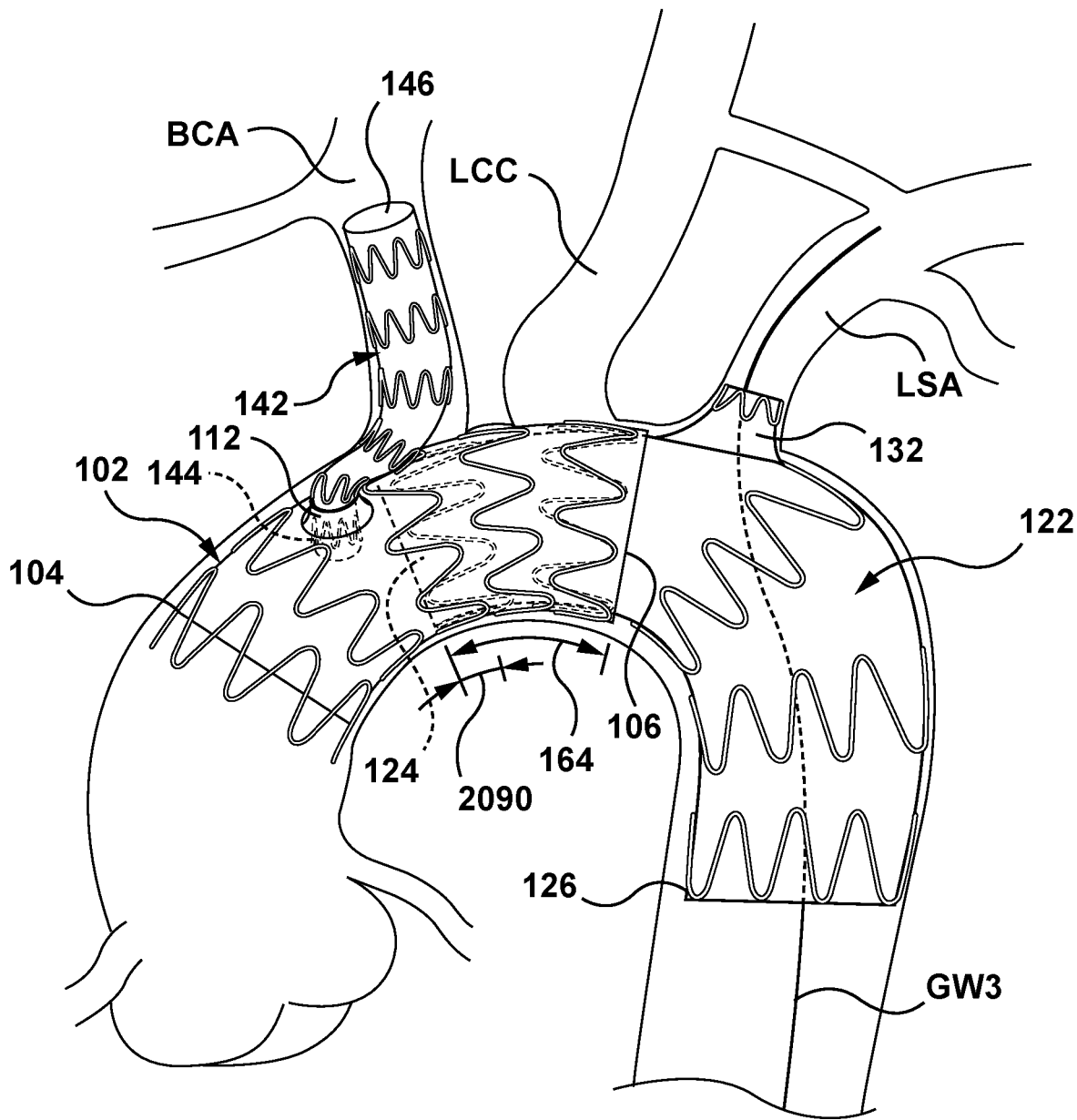

After stent-graft delivery system 1984 is in the location where the coupling 132 of distal aortic stent-graft prosthesis 122 is approximately aligned with the opening into the left subclavian artery LSA, an outer sleeve or sheath of stent-graft delivery system 1984 is retracted proximally to deploy distal aortic stent-graft prosthesis 122 as shown in FIG. 20. More particularly, the outer sleeve or sheath of stent-graft delivery system 1984 may initially be retracted proximally to a position adjacent to coupling 132 to initially only release coupling 132. When coupling 132 extends radially away from an outer surface of graft material 108 as an external coupling, coupling 132 including support wireform 134 provides structural integrity to the top of coupling 132, and orients the distal end of the coupling towards and/or into the ostium of the left subclavian artery LSA. Delivery system 1984 may then be moved and/or rotated to better align coupling 132 with the left subclavian artery LSA. Further, due to the configuration of coupling 132, even if it is not perfectly aligned with the left subclavian artery LSA, the top of the coupling 132 may be moved to properly align its lumen opening with the lumen of the left subclavian artery LSA without having to move the entire distal aortic stent-graft prosthesis 122. Once coupling 132 is deployed and in position in or adjacent to the left subclavian artery LSA, the outer sleeve or sheath of stent-graft delivery system 1984 may be further retracted to deploy the remaining length of distal aortic stent-graft prosthesis 122. Once coupling 132 and distal aortic stent-graft prosthesis 122 are deployed, delivery system 1984 may be removed leaving distal aortic stent-graft prosthesis 122 deployed in situ as shown in FIG. 20. If desired, first guidewire GW1 may be removed at this point of the procedure.

With first branch stent-graft prosthesis 142 proximally rerouting or displacing the ostium of the brachiocephalic artery BCA to the ascending aorta as described above, distal aortic stent-graft prosthesis 122 is deployed with sufficient overlap 164 with respect to proximal aortic stent-graft prosthesis 102. Proximal end 124 of distal aortic stent-graft prosthesis 122 is thus disposed proximal to distal end 106 of proximal aortic stent-graft prosthesis 102, and proximal and distal aortic stent-graft prostheses 102, 122 overlay each other for a portion thereof, thereby forming sufficient overlap 164 to avoid and/or minimize endoleaks between the modular components. Although shown with proximal end 124 of distal aortic stent-graft prosthesis 122 disposed distal to coupling 112 and first branch stent-graft prosthesis 142, proximal end 124 of distal aortic stent-graft prosthesis 122 may be deployed up to proximal end 144 of first branch stent-graft prosthesis 142. Stated another way, proximal end 124 of distal aortic stent-graft prosthesis 122 may be more proximally disposed than shown to increase the amount of sufficient overlap 164 but cannot occlude or block proximal end 144 of first branch stent-graft prosthesis 142 which is providing profusion to the brachiocephalic artery BCA. In such a case, proximal end 124 of distal aortic stent-graft prosthesis 122 may abut against or contact an outer surface of deployed first branch stent-graft prosthesis 142 that is extending internal to proximal aortic stent-graft prosthesis 102. However, since first branch stent-graft prosthesis 142 has a higher radial force than distal aortic stent-graft prosthesis 122 as described herein, distal aortic stent-graft prosthesis 122 does not collapse or otherwise interfere with deployed first branch stent-graft prosthesis 142 and perfusion of the brachiocephalic artery BCA provided thereby.

Notably, when first branch stent-graft prosthesis 142, proximal aortic stent-graft prosthesis 102, and distal aortic stent-graft prosthesis 122 are deployed as shown in FIG. 20, a portion 2090 of the first branch stent-graft prosthesis in its expanded configuration extends along sufficient overlap 164 such that proximal end 144 of first branch stent-graft prosthesis 142 is positioned proximal to sufficient overlap 164 and effectively proximally reroutes the ostium of the brachiocephalic artery BCA. Stated another way, at a cross-section of the deployed aortic arch prosthetic assembly 100 taken within portion 2090, the cross-section includes first branch stent-graft prosthesis 142, proximal aortic stent-graft prosthesis 102, and distal aortic stent-graft prosthesis 122. In this embodiment, first branch stent-graft prosthesis 142 extends external to or outside of proximal aortic stent-graft prosthesis 102 (i.e., portion 2090 of first branch stent-graft prosthesis 142 extends between an outer surface of proximal aortic stent-graft prosthesis 102 and a vessel wall of the aortic arch) and thus first branch stent-graft prosthesis 142 abuts against concentrically disposed proximal and distal aortic stent-graft prostheses 102, 122 along portion 2090. As previously described, however, first branch stent-graft prosthesis 142 is configured to exert a higher radial force than proximal aortic stent-graft prosthesis 102 such that first branch stent-graft prosthesis 142 does not collapse due to the contact with proximal aortic stent-graft prosthesis 102.

Figure 21:
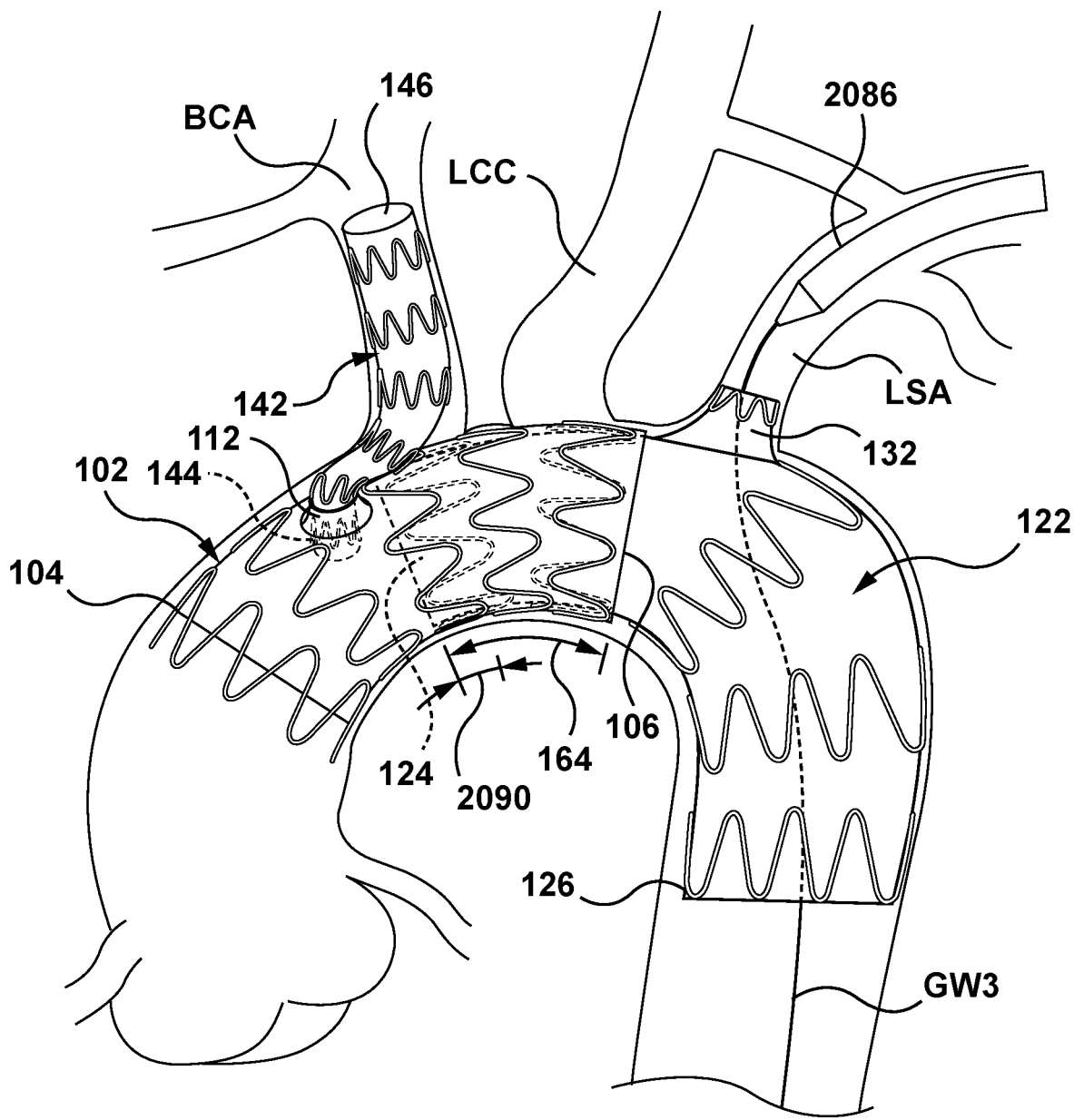
Figure 22:
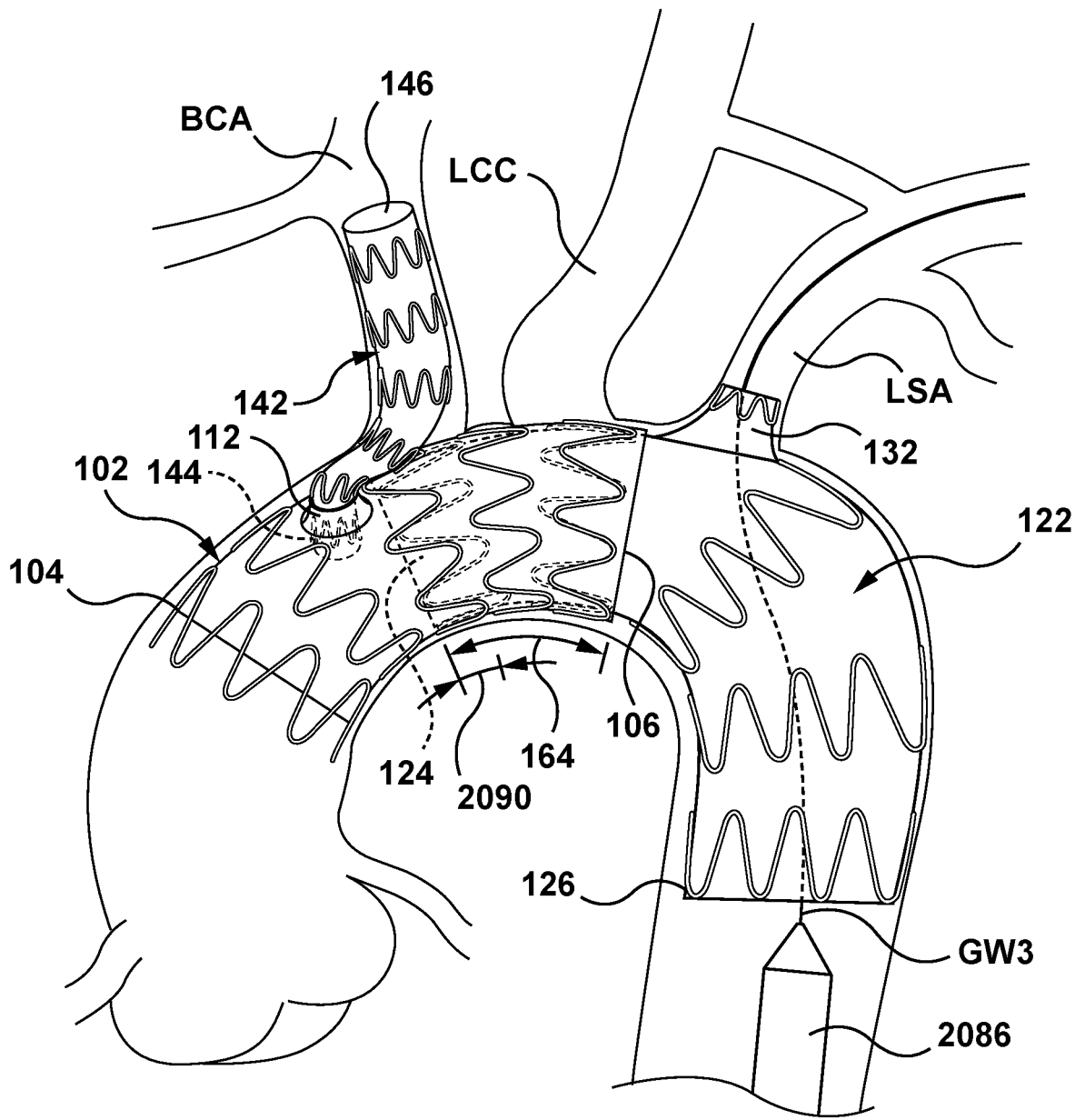

FIG. 21 shows a branch stent-graft delivery system 2086, with second branch stent-graft prosthesis 152 compressed therein, advanced over third guidewire GW3 to the target location in the left subclavian artery LSA and into the descending aorta. The location of the branch stent-graft delivery system 2086 and/or second branch stent-graft prosthesis 152 compressed therein may be verified radiographically and delivery system 2086 and/or second branch stent-graft prosthesis 152 may include radiopaque markers as known in the art. Branch stent-graft delivery system 2086 may be conventional and contains therein second branch stent-graft prosthesis 152. Branch stent-graft delivery system 2086 is advanced into the left subclavian artery LSA such that proximal end 154 of second branch stent-graft prosthesis 152 is disposed within coupling 132. In the embodiment of FIG. 21, branch stent-graft delivery system 2086 is advanced into the left subclavian artery LSA via the radial artery entry point of third guidewire GW3. In another embodiment hereof depicted in FIG. 22, branch stent-graft delivery system 2086 with second branch stent-graft prosthesis 152 compressed therein is delivered into the left subclavian artery LSA via the femoral entry point of third guidewire GW3.

Figure 23:
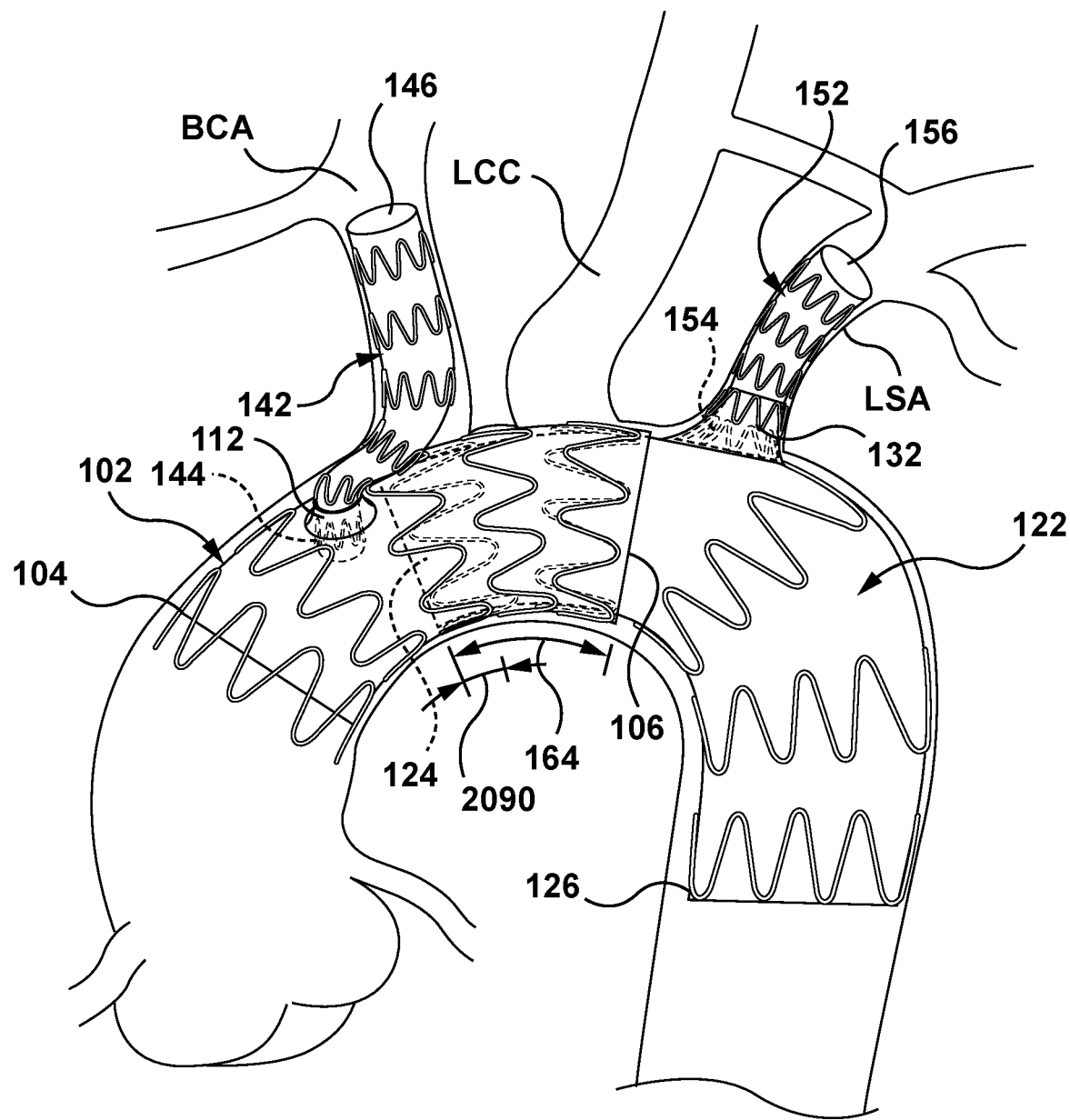

Regardless of which entry point of third guidewire GW3 is utilized, second branch stent-graft prosthesis 152 is advanced over third guidewire GW3 until it is positioned within the left subclavian artery LSA as desired with proximal end 154 of second branch stent-graft prosthesis 152 disposed within coupling 132 of distal aortic stent-graft prosthesis 122. Once second branch stent-graft prosthesis 152 is positioned as desired, an outer sheath of branch stent-graft delivery system 2086 constraining second branch stent-graft prosthesis 152 is then retracted proximally, thereby releasing second branch stent-graft prosthesis 152 from the delivery system. Branch stent-graft delivery system 2086 and third guidewire GW3 are then removed leaving second branch stent-graft prosthesis 152 deployed in situ as shown in FIG. 23. Second branch stent-graft prosthesis 152 now perfuses the left subclavian artery LSA. Although the opening (or ostium) to the left common carotid LCC artery directly from the aortic arch is blocked by aortic arch prosthetic assembly 100, bypass 162 fluidly connects the left common carotid LCC artery to the left subclavian artery LSA and thus perfusion of the left subclavian artery LSA also provides perfusion to the left common carotid LCC artery. Thus, all the great vessels branching off the aortic arch are perfused.

Figure 24:
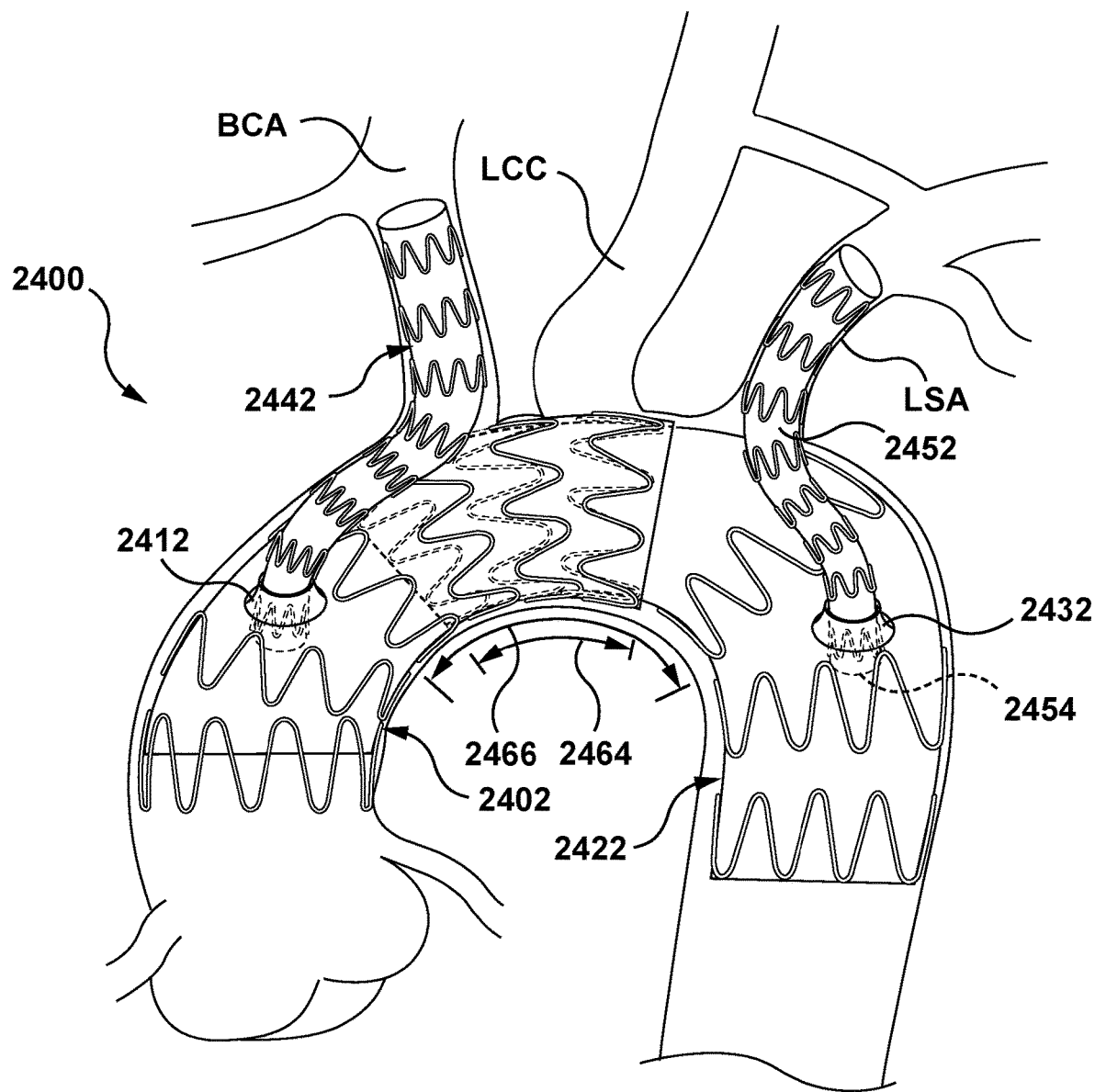
FIG. 24 is a schematic side view of an aortic arch prosthetic assembly according to another embodiment hereof, wherein the aortic arch prosthetic assembly includes a distal aortic stent-graft prosthesis having a coupling that distally reroutes the ostium of the left subclavian artery and the aortic arch prosthetic assembly is shown deployed and assembled in situ within an aortic arch.

FIG. 24 illustrates an alternative embodiment hereof in which the ostium of the left subclavian artery LSA is displaced distally by the second branch stent-graft prosthesis in a manner similar to the way the ostium of the brachiocephalic artery BCA is displaced proximally by the first branch stent-graft prosthesis. The ostium of the left subclavian artery LSA is displaced distally to further increase the amount of achievable overlap of the modular components. An aortic arch prosthetic assembly 2400 is shown deployed and assembled in situ within an aortic arch in FIG. 24. Aortic arch prosthetic assembly 2400 includes a proximal aortic stent-graft prosthesis or module 2402 which is similar to proximal aortic stent-graft prosthesis or module 102, a distal aortic stent-graft prosthesis or module 2422 which is similar to distal aortic stent-graft prosthesis or module 122, a first branch stent-graft prosthesis or module 2442 which is similar to first branch stent-graft prosthesis or module 142, and a second branch stent-graft prosthesis or module 2452. Similar to coupling 112, a coupling 2412 of first or proximal aortic stent-graft prosthesis or module 2402 is purposely positioned or configured to be positioned proximal to the ostium of the brachiocephalic artery. In addition, distal aortic stent-graft prosthesis or module 2422 is similar to distal aortic stent-graft prosthesis or module 122 except that a coupling 2432 thereof is purposely positioned or configured to be positioned in situ distal to the ostium of the left subclavian artery LSA. By purposely positioning coupling 2432 of distal aortic stent-graft prosthesis 2422 to be distal to the ostium of the left subclavian artery LSA when deployed in situ, second branch stent-graft prosthesis 2452 reroutes or displaces the ostium of the left subclavian artery LSA to the descending aorta.

More particularly, aortic arch prosthetic assembly 2400 is configured such that first branch stent-graft prosthesis 2442 proximally reroutes or displaces the ostium of the brachiocephalic artery to the ascending aorta and second branch stent-graft prosthesis 2452 distally reroutes or displaces the ostium of the left subclavian artery LSA to the descending aorta so that distal aortic stent-graft prosthesis 2422 can be deployed with a sufficient overlap 2464 with respect to proximal aortic stent-graft prosthesis 2402. By rerouting or displacing the ostium of the brachiocephalic artery BCA as well as the ostium of the left subclavian artery LSA, aortic arch prosthetic assembly 2400 provides for an endovascular approach that creates or widens the distance for a landing zone 2466 for the deployment of distal aortic stent-graft prosthesis 2422. Landing zone 2466 is greater than landing zone 166 described and shown above with respect to FIG. 2 since landing zone 2466 includes the additional distance gained from distally rerouting or displacing the ostium of the left subclavian artery LSA via second branch stent-graft prosthesis 2452. Landing zone 2466 extends from the proximal end of first branch stent-graft prosthesis 2442 (which is disposed after rerouting thereof in the ascending aorta) to proximal end 2454 of second branch stent-graft prosthesis 2452 (which is disposed after rerouting thereof in the descending aorta).

Figure 25:
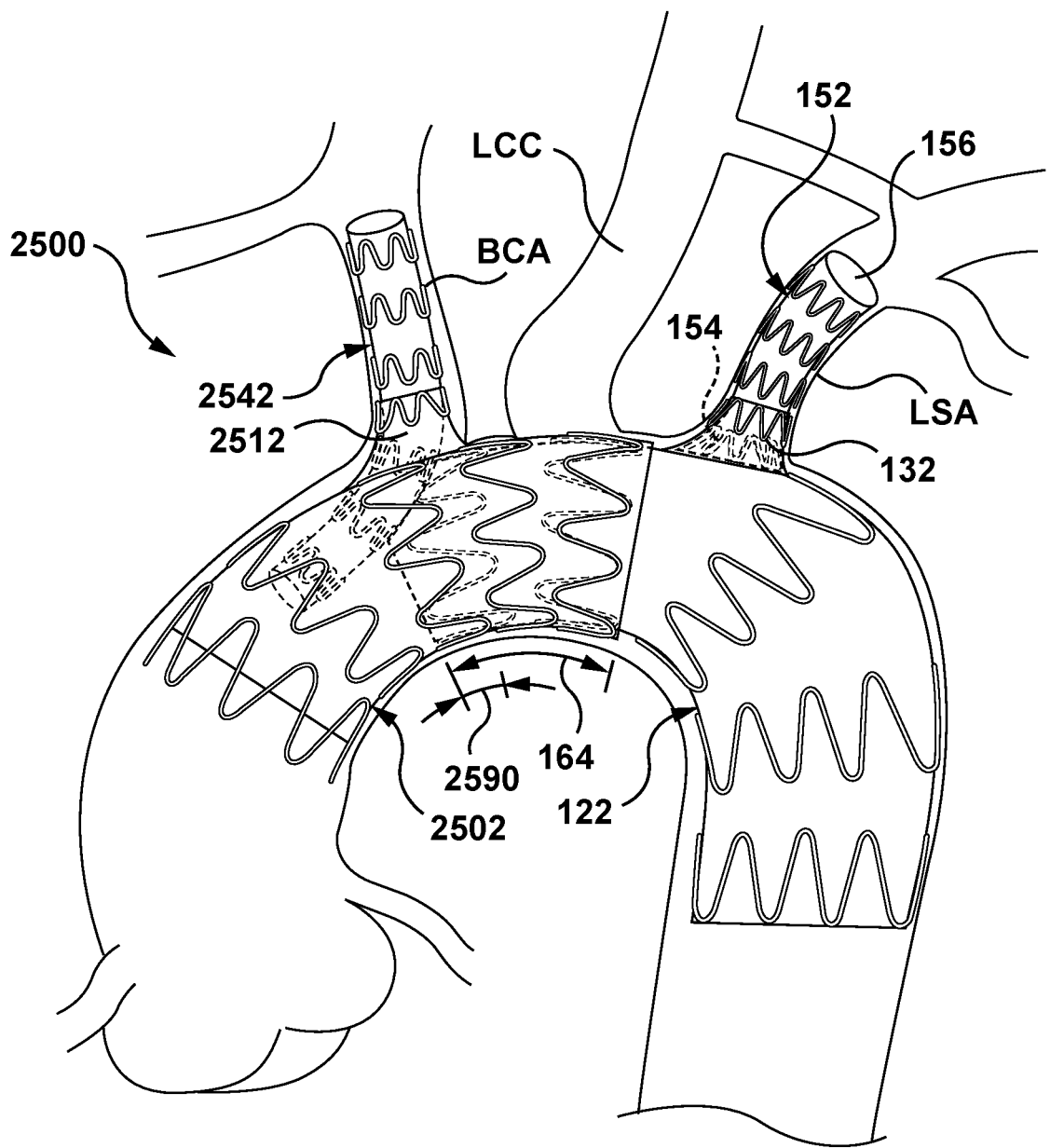
FIG. 25 is a schematic side view of an aortic arch prosthetic assembly according to another embodiment hereof, wherein the aortic arch prosthetic assembly includes a first branch stent-graft prosthesis that extends only internal to a proximal aortic stent-graft prosthesis in order to reroute the ostium of the brachiocephalic artery and wherein the aortic arch prosthetic assembly is shown deployed and assembled in situ within an aortic arch.

FIG. 25 illustrates an alternative embodiment hereof in which the ostium of the brachiocephalic artery BCA is displaced proximally by the first branch stent-graft prosthesis. In previously-described embodiments, at least a portion of the first branch stent-graft prosthesis (first branch stent-graft prosthesis 142) extends external to or outside of the proximal aortic stent-graft prosthesis (proximal aortic stent-graft prosthesis 102) such that this external portion of the first branch stent-graft prosthesis is sandwiched between and contacts both the outer surface of the proximal aortic stent-graft prosthesis and the wall of the aorta. However, in the embodiment of FIG. 25, the first branch stent-graft prosthesis extends only internal to or inside of the proximal aortic stent-graft prosthesis. Stated another way, in the embodiment of FIG. 25, no portion of the first branch stent-graft prosthesis is sandwiched between the outer surface of the proximal aortic stent-graft prosthesis and the wall of the aorta. An aortic arch prosthetic assembly 2500 is shown deployed and assembled in situ within an aortic arch in FIG. 25. Aortic arch prosthetic assembly 2500 includes a proximal aortic stent-graft prosthesis or module 2502 which is similar to proximal aortic stent-graft prosthesis or module 102, distal aortic stent-graft prosthesis or module 122, a first branch stent-graft prosthesis or module 2542 which is similar to first branch stent-graft prosthesis or module 142, and second branch stent-graft prosthesis or module 152. In this embodiment, a coupling 2512 of proximal aortic stent-graft prosthesis 2502 is not purposely positioned or configured to be positioned proximal to the ostium of the brachiocephalic artery. Rather, coupling 2512 is positioned or configured to extend into the ostium of the brachiocephalic artery as shown in FIG. 25. First branch stent-graft prosthesis 2542 is then deployed through coupling 2512 but a relatively longer portion of first branch stent-graft prosthesis 2542 extends within the lumen of proximal aortic stent-graft prosthesis 2502. For example, in an embodiment hereof, approximately 10-30 mm of first branch stent-graft prosthesis 2542 extends within the lumen of proximal aortic stent-graft prosthesis 2502. Distal aortic stent-graft prosthesis 122 is then deployed within the distal portion of proximal aortic stent-graft prosthesis 2502. When deployed, distal aortic stent-graft prosthesis 122 contacts or abuts against the outer surface of a portion of deployed first branch stent-graft prosthesis 2542. However, first branch stent-graft prosthesis 2542 has a higher radial force than distal aortic stent-graft prosthesis 122 and thus distal aortic stent-graft prosthesis 122 does not collapse or otherwise interfere with deployed first branch stent-graft prosthesis 2542 and perfusion of the brachiocephalic artery BCA provided thereby. Distal aortic stent-graft prosthesis 122 conforms to the outer surface of a portion of deployed first branch stent-graft prosthesis 2542 and thus may be partially collapsed by deployed first branch stent-graft prosthesis 2542, but lumen 129 remains at least partially open for blood to flow through distal aortic stent-graft prosthesis 122 due to the relatively smaller size of deployed first branch stent-graft prosthesis 2542.

Notably, when first branch stent-graft prosthesis 2542, proximal aortic stent-graft prosthesis 2502, and distal aortic stent-graft prosthesis 122 are deployed as shown in FIG. 25, a portion 2590 of first branch stent-graft prosthesis 2542 in its expanded configuration extends along sufficient overlap 164 such that a proximal end of first branch stent-graft prosthesis 2542 is positioned proximal to sufficient overlap 164 and effectively proximally reroutes the ostium of the brachiocephalic artery BCA. Stated another way, at a cross-section of the deployed aortic arch prosthetic assembly 2500 taken within portion 2590, the cross-section includes first branch stent-graft prosthesis 2542, proximal aortic stent-graft prosthesis 2502, and distal aortic stent-graft prosthesis 122. In this embodiment, first branch stent-graft prosthesis 2542 extends internal to or inside of proximal aortic stent-graft prosthesis 2502 (i.e., portion 2590 of first branch stent-graft prosthesis 2542 extends within the lumen of proximal aortic stent-graft prosthesis 2502 and abuts against distal aortic stent-graft prosthesis 122) and thus both first branch stent-graft prosthesis 2542 and distal aortic stent-graft prosthesis 122 are radially disposed within proximal aortic stent-graft prosthesis 2502 along portion 2590. As previously described, however, first branch stent-graft prosthesis 2542 is configured to exert a higher radial force than distal aortic stent-graft prosthesis 122 such that first branch stent-graft prosthesis 2542 does not collapse due to the contact with distal aortic stent-graft prosthesis 122.

Figure 26:
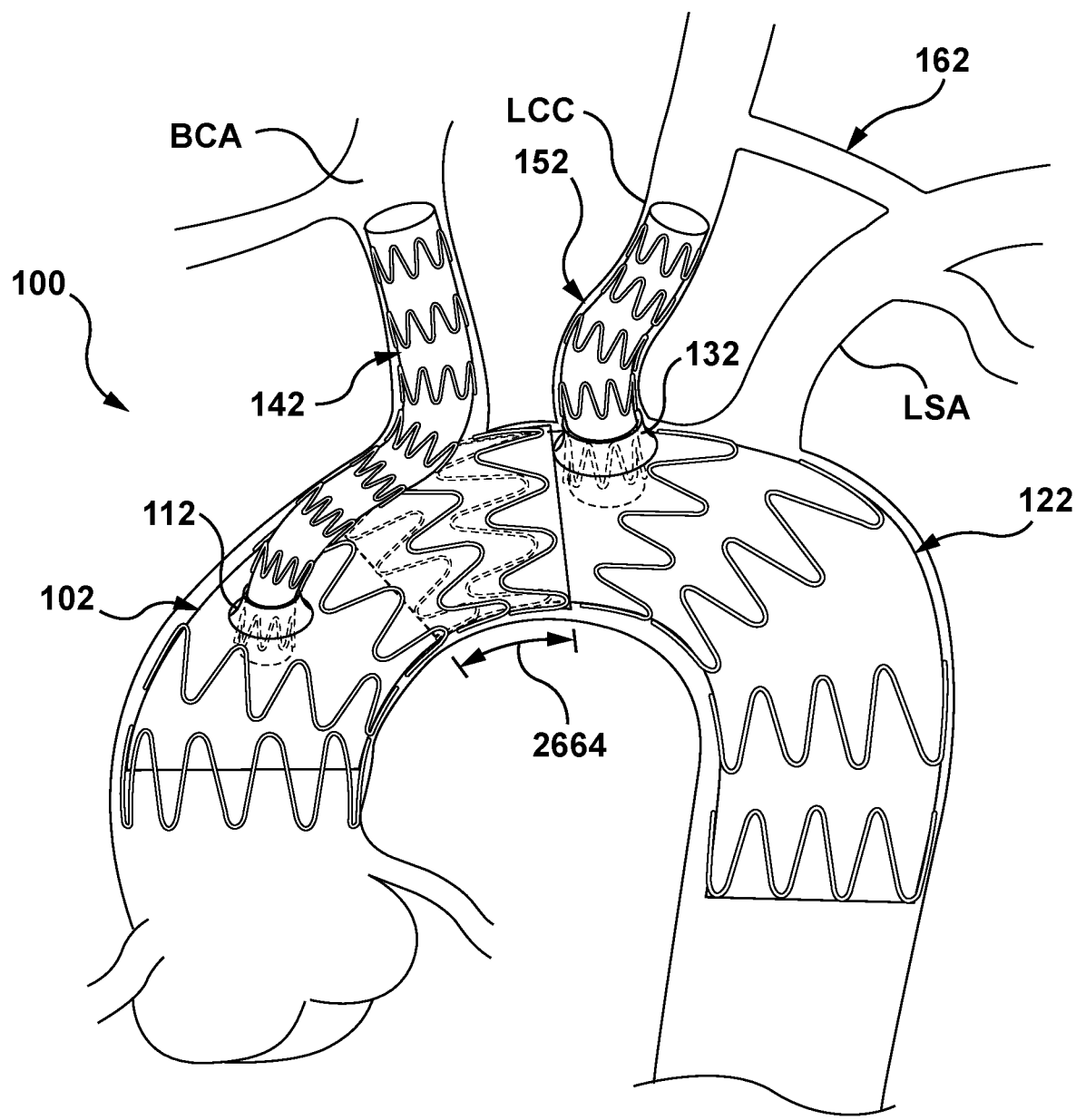
FIG. 26 is a schematic side view of an aortic arch prosthetic assembly according to an embodiment hereof, wherein the aortic arch prosthetic assembly is shown deployed and assembled in situ within an aortic arch and the second branch stent-graft prosthesis thereof is deployed within the left common carotid artery rather than the left subclavian artery.

Although second branch stent-graft prosthesis 152/2452 is described above as providing perfusion to the left subclavian artery LSA, in another embodiment hereof second branch stent-graft prosthesis 152/2452 may be deployed within the left common carotid LCC artery as shown in FIG. 26. As shown in FIG. 26, a sufficient overlap 2664 still occurs between proximal and distal aortic stent-graft prostheses 102, 122 when second branch stent-graft prosthesis 152 is disposed within the left common carotid LCC artery rather than the left subclavian artery LSA. With bypass 162 fluidly connecting the left common carotid LCC artery to the left subclavian artery LSA, perfusion of the left common carotid LCC artery via second branch stent-graft prosthesis 152 also provides perfusion to the left subclavian artery LSA.

Further, in another embodiment hereof, second branch stent-graft prosthesis 152 may an integral extension of distal aortic stent-graft prosthesis 122 rather than a separate module or component of the aortic arch prosthetic assembly.

In the method described in FIGS. 12-23, proximal aortic stent-graft prosthesis or module 102 is deployed or implanted first, followed by deployment of first branch stent-graft prosthesis or module 142, followed by deployment of distal aortic stent-graft prosthesis or module 122, and lastly deployment of second branch stent-graft prosthesis or module 152. This order or sequence prioritizes the establishment of flow and perfusion to the brachiocephalic artery BCA. However, the sequence of deployment of the modules may vary from the order described in FIGS. 12-23. For example, in another embodiment hereof, the modules may be deployed from distal to proximal such that distal aortic stent-graft prosthesis or module 122 is deployed first, followed by deployment of second branch stent-graft prosthesis or module 152, followed by deployment of proximal aortic stent-graft prosthesis or module 102, and lastly deployment of first branch stent-graft prosthesis or module 142. In another embodiment hereof, the aortic stent-graft prostheses (i.e., proximal aortic stent-graft prosthesis or module 102 and distal aortic stent-graft prosthesis or module 122) may both be deployed before the branch stent-graft prostheses (first branch stent-graft prosthesis or module 142 and second branch stent-graft prosthesis or module 152).

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of deploying a prosthetic assembly within an aortic arch, the method comprising the steps of:
    advancing a first delivery system over a first guidewire and a second guidewire, the first guidewire pre-disposed within the aortic arch and the second guidewire pre-disposed within the brachiocephalic artery, wherein the first delivery system includes a proximal aortic stent-graft prosthesis disposed on a distal portion thereof and the proximal aortic stent-graft prosthesis is in a compressed configuration for delivery;
    deploying the proximal aortic stent-graft prosthesis into an expanded configuration within a proximal portion of the aortic arch, wherein a coupling of the proximal aortic stent-graft prosthesis is disposed proximal to the ostium of the brachiocephalic artery, the coupling being frustoconically shaped and including an annular support wireform attached to and extending around an unattached end of the coupling,
    advancing a second delivery system over the second guidewire, wherein second delivery system includes a first branch stent-graft prosthesis disposed on a distal portion thereof and the first branch stent-graft prosthesis is in a compressed configuration for delivery;
    deploying the first branch stent-graft prosthesis into an expanded configuration within the brachiocephalic artery and through the coupling of the proximal aortic stent-graft prosthesis;
    advancing a third delivery system over at least the first guidewire, wherein the third delivery system includes a distal aortic stent-graft prosthesis disposed on a distal portion thereof and the distal aortic stent-graft prosthesis is in a compressed configuration for delivery;
    deploying the distal aortic stent-graft prosthesis into an expanded configuration within a distal portion of the aortic arch, wherein a proximal end of the distal aortic stent-graft prosthesis is disposed within the distal end of the proximal aortic stent-graft prosthesis to form an overlap between the proximal and distal aortic stent-graft prostheses.

2. The method of claim 1, wherein the second guidewire extends from a brachial entry point to a femoral entry point.

3. The method of claim 2, wherein the second delivery system is advanced into the brachiocephalic artery via the brachial entry point of the second guidewire.

4. The method of claim 2, wherein the second delivery system is advanced into the brachiocephalic artery via the femoral entry point of the second guidewire.

5. The method of claim 1, wherein further comprising the step of repositioning the second guidewire after the step of deploying the first branch stent-graft prosthesis, and wherein the third delivery system is delivered over the first guidewire and the second guidewire after the step of repositioning.

6. The method of claim 1, further comprising the step of removing the second guidewire after the step of deploying the first branch stent-graft prosthesis.

7. The method of claim 1, wherein the third delivery system is delivered over the first guidewire and a third guidewire, the third guidewire extending from a radial artery entry point to a femoral entry point.

8. The method of claim 7, further comprising positioning a second branch stent-graft prosthesis within a branch vessel and through a coupling of the distal aortic stent-graft prosthesis, wherein the second branch stent-graft prosthesis is advanced into the branch vessel via the radial artery entry point of the third guidewire.

9. The method of claim 7, further comprising positioning a second branch stent-graft prosthesis within a branch vessel and through a coupling of the distal aortic stent-graft prosthesis, wherein the second branch stent-graft prosthesis is advanced into the branch vessel via the femoral entry point of the third guidewire.

10. The method of claim 1, wherein the coupling of the proximal aortic stent-graft prosthesis includes an unsupported portion of a graft material extending between the annular support wireform and a base of the coupling.

11. The method of claim 10, wherein upon deployment the coupling of the proximal aortic stent-graft prosthesis extends radially outwards to orient the unattached end of the coupling towards the vessel wall of the aorta.

12. The method of claim 10, wherein the annular support wireform has a sinusoidal configuration.

13. The method of claim 10, wherein a height of the annular support wireform is between 25% and 33% of a height of the coupling.

14. The method of claim 1, wherein the distal aortic stent-graft prosthesis includes a coupling, the coupling being frustoconical shaped and including an annular support wireform attached to and extending around an unattached end of the coupling.

15. The method of claim 14, wherein upon deployment the coupling of the distal stent-graft prosthesis is disposed adjacent to the ostium of the left subclavian artery and the method further comprises positioning a second branch stent-graft prosthesis within the left subclavian artery and through the coupling of the distal aortic stent-graft prosthesis, wherein the second branch stent-graft prosthesis is in a compressed configuration for delivery; and deploying the second branch stent-graft prosthesis into an expanded configuration.

16. The method of claim 15, wherein the coupling of the distal aortic stent-graft prosthesis is positioned within the ostium of the left subclavian artery after the step of deploying the distal aortic stent-graft prosthesis.

17. The method of claim 15, wherein the coupling of the distal aortic stent-graft prosthesis is positioned distal to the ostium of the left subclavian artery after the step of deploying the distal aortic stent-graft prosthesis.

18. The method of claim 14, wherein upon deployment the coupling of the distal stent-graft prosthesis is disposed adjacent to the ostium of the left common carotid artery and the method further comprises positioning a second branch stent-graft prosthesis within the left common carotid artery and through the coupling of the distal aortic stent-graft prosthesis, wherein the second branch stent-graft prosthesis is in a compressed configuration for delivery; and deploying the second branch stent-graft prosthesis into an expanded configuration.

19. The method of claim 18, wherein the coupling of the distal aortic stent-graft prosthesis is positioned within the ostium of the left common carotid artery after the step of deploying the distal aortic stent-graft prosthesis.

20. The method of claim 7, wherein the coupling of the distal aortic stent-graft prosthesis is positioned distal to the ostium of the left common carotid artery after the step of deploying the distal aortic stent-graft prosthesis.

* * * * *